United States Patent
Komoto et al.

(10) Patent No.: US 11,701,440 B2
(45) Date of Patent: Jul. 18, 2023

(54) MODIFIED ANTIBODY AND RADIOACTIVE METAL-LABELLED ANTIBODY

(71) Applicants: NIHON MEDI-PHYSICS CO., LTD., Tokyo (JP); National University Corporation Kagoshima University, Kagoshima (JP); National University Corporation Chiba University, Chiba (JP)

(72) Inventors: Shota Komoto, Tokyo (JP); Yu Ogawa, Tokyo (JP); Yoshinari Shoyama, Tokyo (JP); Tadashi Hatano, Tokyo (JP); Yuji Ito, Kagoshima (JP); Yasushi Arano, Chiba (JP); Hiroyuki Suzuki, Chiba (JP); Tomoya Uehara, Chiba (JP)

(73) Assignees: NIHON MEDI-PHYSICS CO., LTD., Tokyo (JP); NATIONAL UNIVERSITY CORPORATION KAGOSHIMA UNIVERSITY, Kagoshima (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 0 days.

(21) Appl. No.: 17/047,859

(22) PCT Filed: Apr. 15, 2019

(86) PCT No.: PCT/JP2019/016156
§ 371 (c)(1),
(2) Date: Oct. 15, 2020

(87) PCT Pub. No.: WO2019/203191
PCT Pub. Date: Oct. 24, 2019

(65) Prior Publication Data
US 2021/0170058 A1 Jun. 10, 2021

(30) Foreign Application Priority Data
Apr. 16, 2018 (JP) .................. 2018-078487

(51) Int. Cl.
*A61K 47/68* (2017.01)
*A61K 51/10* (2006.01)
(Continued)

(52) U.S. Cl.
CPC ...... *A61K 51/1093* (2013.01); *A61K 47/6887* (2017.08); *A61K 47/6889* (2017.08);
(Continued)

(58) Field of Classification Search
CPC ............ A61K 47/6887; A61K 47/6889; A61K 51/0482; A61K 51/088; A61K 51/1045;
(Continued)

(56) References Cited

U.S. PATENT DOCUMENTS 10,866,235 B2 * 12/2020 Soskic ............. G01N 33/54366
11,167,050 B2 * 11/2021 Arano .................. C07K 5/0812
(Continued)

FOREIGN PATENT DOCUMENTS

JP 2015086213 A 5/2015
JP 2017518975 A 7/2017
(Continued)

OTHER PUBLICATIONS

Extended European Search Report dated May 19, 2021, issued by the European Patent Office in corresponding European Application No. 19787597.4-1109. (7 pages).
Arano, Y., et al. "Chemical Design of Radiolabeled Antibody Fragments for Low Renal Radioactivity Levels," Cancer Research, vol. 59, pp. 128-134 (Jan. 1, 1999).
Axup, J.Y., et al., "Synthesis of site-specific antibody-drug conjugates using unnatural amino acids," Proceedings of the National Academy of Sciences of the United States of America, vol. 109, No. 40, pp. 16101-16106 (Oct. 2, 2012).
Bernardes, G.J., et al., "Site-specific chemical modification of antibody fragments using traceless cleavable linkers," Nature Protocols, vol. 8, No. 11, pp. 2079-2089 (Oct. 3, 2013).
(Continued)

Primary Examiner — Jeffrey E. Russel
(74) Attorney, Agent, or Firm — Buchanan Ingersoll & Rooney PC

(57) ABSTRACT

Described is a labeling technique which can facilitate the metabolism in the liver after administration to patients without the reduction in the antibody function, thereby reducing accumulation of radionuclides in an organ such as the liver, and a modified antibody containing an IgG antibody and an IgG-binding peptide bound to the IgG antibody. The IgG-binding peptide has an amino acid sequence consisting of 13 to 17 amino acid residues, such as GPDCAYH (Xaa1)GELVWCTFH (SEQ ID NO: 2) wherein Xaa1 represents a lysine residue, a cysteine residue, an aspartic acid residue, a glutamic acid residue, 2-aminosuberic acid, or diaminopropionic acid, and a compound represented by the following formula (II-1) is linked at a position of the lysine residue via a modification linker to the N terminus of the IgG-binding peptide.

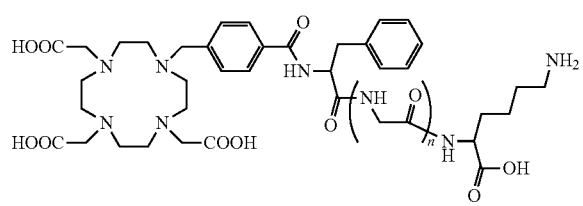

(II-1)

10 Claims, 3 Drawing Sheets

Specification includes a Sequence Listing.

(51) Int. Cl.

| | | |
|---|---|---|
| C07K 5/065 | (2006.01) | |
| C07K 5/087 | (2006.01) | |
| A61K 51/04 | (2006.01) | |
| A61K 51/08 | (2006.01) | |
| C07D 257/02 | (2006.01) | |
| C07K 7/08 | (2006.01) | |
| C07K 16/32 | (2006.01) | |

(52) U.S. Cl.
CPC ........ *A61K 51/0482* (2013.01); *A61K 51/088* (2013.01); *A61K 51/1096* (2013.01); *C07D 257/02* (2013.01); *C07K 5/06078* (2013.01); *C07K 5/0812* (2013.01); *C07K 7/08* (2013.01); *C07K 16/32* (2013.01); *C07K 2317/21* (2013.01)

(58) Field of Classification Search
CPC ............ A61K 51/1093; A61K 51/1096; C07K 5/06078; C07K 5/0812
See application file for complete search history.

(56) References Cited

U.S. PATENT DOCUMENTS

| | | | |
|---|---|---|---|
| 2018/0141976 | A1 | 5/2018 | Ito |
| 2019/0091353 | A1 | 3/2019 | Arano et al. |
| 2020/0181196 | A1 | 6/2020 | Ito et al. |
| 2020/0268913 | A1 | 8/2020 | Arano et al. |
| 2021/0000912 | A1* | 1/2021 | Agrez .................... A61P 29/02 |

FOREIGN PATENT DOCUMENTS

| | | | |
|---|---|---|---|
| WO | 2013081091 A1 | 6/2013 | |
| WO | 2015175357 A1 | 11/2015 | |
| WO | 2016186206 A1 | 11/2016 | |
| WO | 2017150549 A1 | 9/2017 | |
| WO | 2017217347 A1 | 12/2017 | |
| WO | 2019065774 A1 | 4/2019 | |

OTHER PUBLICATIONS

International Search Report (with English translation) and Written Opinion dated Jul. 9, 2019, in corresponding International Patent Application No. PCT/JP2019/016156. (11 pages).

Rodwell, J.D. et al., "Site-specific covalent modification of monoclonal antibodies: In vitro and in vivo evaluations," Proceedings of the National Academy of Sciences of the United States of America, vol. 83, pp. 2632-2636 (Apr. 1986).

Shen, B-Q., et al., Conjugation site modulates the in vivo stability and therapeutic activity of antibody-drug conjugates, Nature Biotechnology, vol. 30, No. 2, pp. 184-189 (Feb. 2012).

Tian, F., et al., A general approach to site-specific antibody drug conjugates, Proceedings of the National Academy of Sciences of the United States of America, vol. 111, No. 5, pp. 1766-1771 (Feb. 4, 2014).

Uehara, T., et al. "Design, Synthesis, and Evaluation of [$^{188}$Re] Organorhenium-Labeled Antibody Fragments with Renal Enzyme-Cleavable Linkage for Low Renal Radioactivity Levels," Bioconjugate Chemistry, vol. 18, No. 1, pp. 190-198 (Dec. 22, 2006).

Uchimura, O.M., et al., "Novel Dota Derivative Giving Stable $^{68}$GA Complex In Vivo," The Pharmaceutical Society of Japan, vol. 138, 3 pp. (Mar. 2018).

Zimmerman, E.S., et al., "Production of Site-Specific Antibody—Drug Conjugates Using Optimized Non-Natural Amino Acids in a Cell-Free Expression System," Bioconjugate Chemistry, vol. 25, pp. 351-361 (2014).

Notification of Transmittal of Translation of the International Preliminary Report on Patentability and English Translation of the Written Opinion dated Oct. 20, 2020, by the International Bureau of WIPO in corresponding International Patent Application No. PCT/JP2019/016156. (8 pages).

Office Action (Notice of Reasons for Refusal) dated Mar. 1, 2023, by the Japanese Patent Office in corresponding Japanese Patent Application No. 2020-514375, and an English translation of the Office Action. (10 pages).

* cited by examiner

1-HOUR POINT AFTER ADMINISTRATION (%ID)

6-HOUR POINT AFTER ADMINISTRATION (%ID)

CHANGES WITH TIME (KIDNEY, %ID)

CHANGES WITH TIME

SEQUENCE LISTING

<160> NUMBER OF SEQ ID NOS: 6

<210> SEQ ID NO 1
<211> LENGTH: 13
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 1

Asp Cys Ala Tyr His Xaa Gly Glu Leu Val Trp Cys Thr
1               5                   10

<210> SEQ ID NO 2
<211> LENGTH: 17

```
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 2

Gly Pro Asp Cys Ala Tyr His Xaa Gly Glu Leu Val Trp Cys Thr Phe
1               5                   10                  15

His

<210> SEQ ID NO 3
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 3

Arg Gly Asn Cys Ala Tyr His Xaa Gly Gln Leu Val Trp Cys Thr Tyr
1               5                   10                  15

His

<210> SEQ ID NO 4
<211> LENGTH: 17
<212> TYPE: PRT
<213> ORGANISM: Artificial
<220> FEATURE:
<223> OTHER INFORMATION: IgG-binding peptide
<220> FEATURE:
<221> NAME/KEY: misc_feature
<222> LOCATION: (2)..(2)
<223> OTHER INFORMATION: Xaa is homocysteine
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid
<220> FEATURE:
<221> NAME/KEY: misc_feature
<222> LOCATION: (16)..(16)
<223> OTHER INFORMATION: Xaa is homocysteine

<400> SEQUENCE: 4

Gly Xaa Asp Cys Ala Tyr His Xaa Gly Glu Leu Val Trp Cys Thr Xaa
1               5                   10                  15

His

<210> SEQ ID NO 5
<211> LENGTH: 110
<212> TYPE: PRT
<213> ORGANISM: Homo Sapiens

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30
```

```
Val Val Asp Val Ser His Glu Asp Pro Glu Val Lys Phe Asn Trp Tyr
            35              40              45

Val Asp Gly Val Glu Val His Asn Ala Lys Thr Lys Pro Arg Glu Glu
 50              55              60

Gln Tyr Asn Ser Thr Tyr Arg Val Val Ser Val Leu Thr Val Leu His
 65              70              75              80

Gln Asp Trp Leu Asn Gly Lys Glu Tyr Lys Cys Lys Val Ser Asn Lys
                85              90              95

Ala Leu Pro Ala Pro Ile Glu Lys Thr Ile Ser Lys Ala Lys
                100             105             110

<210> SEQ ID NO 6
<211> LENGTH: 17
<212> TYPE: PRT
<213> ORGANISM: Artificial Sequence
<220> FEATURE:
<223> OTHER INFORMATION: IgG-binding peptide
<220> FEATURE:
<221> NAME/KEY: MISC_FEATURE
<222> LOCATION: (1)..(1)
<223> OTHER INFORMATION: Xaa is an amino acid residue other than
      cysteine
<220> FEATURE:
<221> NAME/KEY: MISC_FEATURE
<222> LOCATION: (2)..(3)
<223> OTHER INFORMATION: Xaa is an amino acid residue other than
      cysteine or is absent
<220> FEATURE:
<221> NAME/KEY: MISC_FEATURE
<222> LOCATION: (5)..(6)
<223> OTHER INFORMATION: Xaa is an amino acid residue other than
      cysteine
<220> FEATURE:
<221> NAME/KEY: MISC_FEATURE
<222> LOCATION: (8)..(8)
<223> OTHER INFORMATION: Xaa is lysine, cysteine, aspartic acid,
      glutamic acid, 2-aminosuberic acid, or diaminopropionic acid
<220> FEATURE:
<221> NAME/KEY: MISC_FEATURE
<222> LOCATION: (10)..(10)
<223> OTHER INFORMATION: Xaa is glutamic acid, glutamine, or asparagine
<220> FEATURE:
<221> NAME/KEY: MISC_FEATURE
<222> LOCATION: (15)..(16)
<223> OTHER INFORMATION: Xaa is an amino acid residue other than
      cysteine or is absent
<220> FEATURE:
<221> NAME/KEY: MISC_FEATURE
<222> LOCATION: (17)..(17)
<223> OTHER INFORMATION: Xaa is an amino acid residue other than
      cysteine

<400> SEQUENCE: 6

Xaa Xaa Xaa Cys Xaa Xaa His Xaa Gly Xaa Leu Val Trp Cys Xaa Xaa
 1               5              10              15

Xaa
```

MODIFIED ANTIBODY AND RADIOACTIVE METAL-LABELLED ANTIBODY

CROSS REFERENCE OF RELATED APPLICATIONS

This application claims the priority based on Japanese Patent Application No. 2018-78487 filed on Apr. 16, 2018, the disclosure of which is incorporated herein by reference in its entirety.

SEQUENCE LISTING

Incorporated by reference herein in its entirety is a computer-readable sequence listing submitted via EFS-Web and identified as follows: One (4,112 byte ASCII (Text)) file named "20221127 updated sequence listing" created on Nov. 27, 2022.

TECHNICAL FIELD

The present invention relates to modification and radioactive metal labeling of an IgG antibody.

BACKGROUND ART

Antibodies are used for detection of target molecules in various research and development due to the specificity for target molecules, and in the field of medical care, an antibody that specifically binds to an affected site of cancer or the like is labeled with a radionuclide and is administered into the body for diagnosis with single photon emission computed tomography (SPECT) or positron emission tomography (PET). Further, the antibody labeled with a radionuclide has also been noticed as a pharmaceutical for treating diseases.

As a method for labeling an antibody with a radionuclide, a method has been used in which a chelate compound is bound to an antibody, and a radioactive metal element is supported on the chelate compound (Non Patent Literature 1). The binding of such a chelate compound has been performed so far mainly via an amino group of lysine, a thiol group of cysteine, an activated carboxyl group or the like that is contained in an antibody, but the binding is not site-specific even though specific to a functional group, and therefore, for example, there has been a problem that the antibody is decreased in activity by a modification or the like of the antibody at an antigen-binding site, or a problem that the number of compounds to be bound is difficult to control.

In order to overcome such a problem, modification of an antibody has been performed by using an antibody in which a specific functional group has been site-specifically introduced. For example, a modification at a specific site has been made possible by introducing an unnatural amino acid (Non Patent Literatures 2 to 4) or a free cysteine (Non Patent Literatures 5 and 6) into a specific site by genetic engineering modification. Even though site-specific antibody modification techniques have been developed as described above, many of them require the antibody itself to be modified by antibody engineering, and it cannot necessarily be said that they are advantageous methods in consideration of reduction in antibody function and high development cost which are associated with the modification.

In view of this, as a method that can specifically and easily modify an antibody, a method has been proposed in which IgG is labeled with a radioactive metal nuclide by linking a ligand to an IgG-binding peptide having a binding ability to a specific site of the Fc domain of an IgG antibody, and binding the IgG-binding peptide to the antibody, without any necessity of modification to the sequence of the antibody molecule, that is, without the functional reduction associated with the genetic modification of the antibody molecule (Patent Literatures 1 and 2).

On the other hand, when a low-molecular weight polypeptide labeled with a radioactive metal nuclide is administered to a living body, radioactivity is observed in kidney for a long time from the early stage after the administration, and therefore, there is a fear that the administration of the radioactive metal-labeled antibody into a living body causes radiation exposure of kidney and renal disorder, but a radiolabeled compound in which a specific low-molecular weight polypeptide is used to reduce the non-specific kidney accumulation has been proposed (Patent Literatures 3 and 4, and Non Patent Literatures 7 and 8).

CITATION LIST

Patent Literature

Patent Literature 1: WO 2017/217347 A
Patent Literature 2: WO 2016/186206 A
Patent Literature 3: WO 2013/081091 A
Patent Literature 4: WO 2017/150549 A

Non Patent Literature

Non Patent Literature 1: Rodwell, J. D. et al., Proceedings of the National Academy of Sciences of the United States of America, 1986, 83, pp. 2632-2636
Non Patent Literature 2: Axup, J. Y. et al., Proceedings of the National Academy of Sciences of the United States of America, 2012, 109, pp. 16101-16106
Non Patent Literature 3: Tian, F. et al., Proceedings of the National Academy of Sciences of the United States of America, 2014, 111, pp. 1766-1771
Non Patent Literature 4: Zimmerman, E. S. et al., Bioconjugate chemistry, 2014, 25, pp. 351-361
Non Patent Literature 5: Shen, B. Q. et al., Nature biotechnology, 2012, 30, pp. 184-189
Non Patent Literature 6: Bernardes, G. J. et al., Nature protocols, 2013, 8, pp. 2079-2089
Non Patent Literature 7: Arano, Yasushi, et al. "Chemical design of radiolabeled antibody fragments for low renal radioactivity levels" Cancer research 59.1 (1999): 128-134

Non Patent Literature 8: Uehara, Tomoya, et al. "Design, synthesis, and evaluation of [$^{188}$Re] organorhenium-labeled antibody fragments with renal enzyme-cleavable linkage for low renal radioactivity levels" Bioconjugate chemistry 18.1 (2007): 190-198.

SUMMARY OF INVENTION

Conventionally, when a radioactive metal-labeled antibody is administered in a living body, high accumulation has been observed in an organ with the reticuloendothelial system being developed, such as liver or spleen, and there has been a concern that the administration may cause unnecessary radiation exposure of normal organs of patients. In the techniques of Patent Literatures 3 and 4, the accumulation in kidney has been reduced, but there has been a concern that the antibody function may be reduced due to the binding to a Fab fragment.

The present invention has been made in view of the above-mentioned circumstances, and is to provide a labeling technique which can facilitate the metabolism in the liver after administration to patients without the reduction in the antibody function, thereby reducing the accumulation of radionuclides in an organ such as the liver.

One aspect of the present invention is to provide a modified antibody including an IgG antibody, and an IgG-binding peptide bound to the IgG antibody, in which the IgG-binding peptide has an amino acid sequence represented by the following formula (I) which consists of 13 to 17 amino acid residues, and has a compound represented by the following formula (II-1) that is linked at a position of the lysine residue thereof via a modification linker to the N terminus of the IgG-binding peptide.

(X$_{1-3}$)-C-(X$_2$)-H-(Xaa1)-G-(Xaa2)-L-V-W-C-(X$_{1-3}$)(SEQ ID NO: 6),

In the formula (I), each X independently represents an amino acid residue other than cysteine, C represents a cysteine residue, H represents a histidine residue, Xaa1 represents a lysine residue, a cysteine residue, an aspartic acid residue, a glutamic acid residue, 2-aminosuberic acid, or diaminopropionic acid, G represents a glycine residue, Xaa2 represents a glutamic acid residue, a glutamine residue, or an asparagine residue, L represents a leucine residue, V represents a valine residue, and W represents a tryptophan residue, and the two cysteine residues may be disulfide-bonded or bound to each other via a linker, and the C terminus may be amidated.

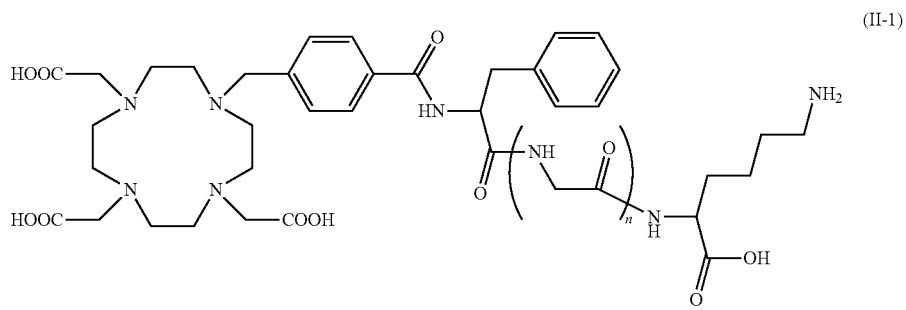

(II-1)

In the formula (II-1), n is 0 or 1.

Another aspect of the present invention is to provide a radioactive metal-labeled antibody including the above-described modified antibody to which a radioactive metal is coordinated, and a radiopharmaceutical including the radioactive metal-labeled antibody.

Another aspect of the present invention is to provide a modified IgG-binding peptide including an IgG-binding peptide having an amino acid sequence represented by the above formula (I) which consists of 13 to 17 amino acid residues, and a modification linker represented by the following formula (III) that is bound to the N terminus of the IgG-binding peptide, and to provide an IgG antibody to which the modified IgG-binding peptide is bound.

L$_1$-L$_2$-L$_3$ (III)

In the formula (III),

L$_1$ represents a polyethylene glycol linker bound to the N terminus of the IgG-binding peptide, L$_2$ represents an amino acid sequence consisting of 0 or more and 5 or less amino acid residues, and L$_3$ represents a group having a DBCO (dibenzocyclooctyne) group at the terminus.

The modified IgG-binding peptide and the IgG antibody to which the modified IgG-binding peptide is bound make it possible to link a ligand to the modified IgG-binding peptide or the IgG antibody by the click reaction by use of a ligand having an azido group that can bind to DBCO by a click reaction.

Further, another aspect of the present invention is to provide a compound represented by the following formula (II), or a salt thereof.

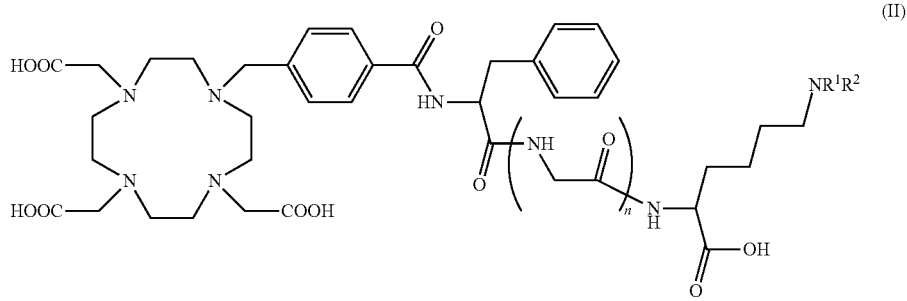

(II)

In the formula (II), n is 0 or 1, $R^1$ and $R^2$ both represent a hydrogen atom, or one of $R^1$ and $R^2$ represents a hydrogen atom and the other represents a group represented by $CO(CH_2)_m N_3$ wherein m is an integer of 1 to 10, or both form a maleimide group or isothiocyanate group together with the nitrogen atom.

The compound of the above formula (II) can bind to a functional group of a protein such as an IgG antibody, or an IgG-binding peptide via a group represented by $NR^1R^2$ at the terminus of the side chain of lysine, and therefore, the compound can be used for radioactive metal labeling of various kinds of target molecules including IgG antibodies. Accordingly, another aspect of the present invention is to provide a compound comprising the compound of the above formula (II) to which a polypeptide to be bound to a target molecule is bound, or a salt thereof.

According to the present invention, an antibody is provided in the Fc region thereof with an excretion promoting linker having a phenylalanine residue and a lysine residue, and therefore a radioactive metal-labeled antibody is obtained which is metabolized in the liver to promote the excretion of radioactive metals from the body and thus is excellent in pharmacokinetics.

DESCRIPTION OF EMBODIMENTS

<Modified IgG-Binding Peptide>

Figure 1A:
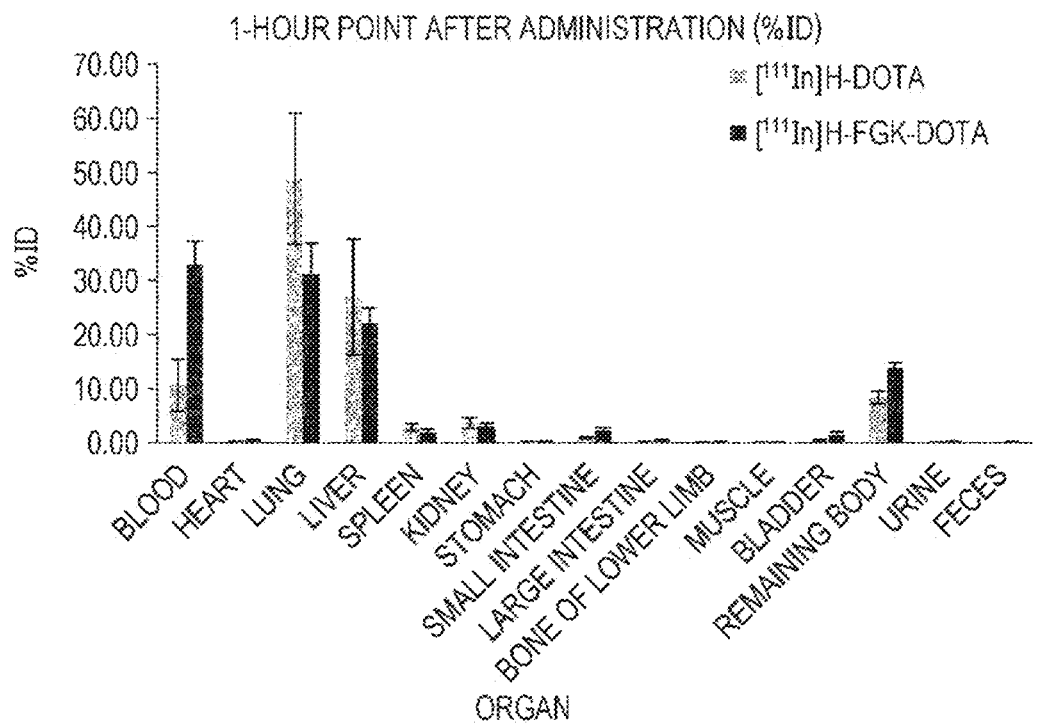
FIG. 1A is a diagram showing an average value and a standard deviation of the radioactivity distribution (% injected dose (ID)) at the 1-hour point after the administration of [$^{111}$In]H-FGK-DOTA and [$^{111}$In]H-DOTA.

In one aspect of the present invention, the modified IgG-binding peptide contains an IgG-binding peptide represented by the above formula (I) which consists of 13 to 17 amino acid residues, and further the N terminus of the IgG-binding peptide is modified with a DBCO linker represented by the above formula (III).

The IgG-binding peptide of the formula (I) is not particularly limited as long as it binds to IgG, and as the IgG-binding peptide, an IgG-binding peptide disclosed in WO 2017/217347 is preferred.

The IgG-binding peptide used in the present invention will be described in detail below.

The "IgG" used in the present specification refers to IgG of a mammal, for example, a primate such as a human, or a chimpanzee, an experimental animal such as a rat, a mouse, or a rabbit, a livestock animal such as a pig, a bovine, a horse, a sheep, or a goat, or a pet animal such as a dog, or a cat, and preferably IgG (IgG1, IgG2, IgG3, or IgG4) of a human. The IgG in the present specification is more preferably human IgG1, IgG2, or IgG4, or rabbit IgG, and particularly preferably human IgG1, IgG2, or IgG4.

The IgG-binding peptide used in the present invention has an amino acid sequence represented by the above formula (I) which comprising of 13 to 17 amino acid residues, and further the IgG-binding peptide can bind to human IgG.

In the above formula (I), the expression "$X_{1-3}$" at the N terminus or C terminus means 1 to 3 consecutive amino acid residues which are each independently any amino acid residue X other than cysteine (C or Cys), in which the constituent amino acid residues are the same as or different from one another, and preferably have any sequence excluding the case where all the 3 residues are the same. Similarly, the expression "$X_2$" means 2 consecutive amino acid residues which are each independently any amino acid X other than cysteine (C or Cys), in which the constituent amino acid residues are the same as or different from each other, and preferably have any sequence excluding the case where the consecutive 2 amino acid residues are the same.

The 2 cysteine residues in the formula (I) can be disulfide-bonded to form a cyclic peptide. In general, in the IgG-binding peptide of the formula (I), 2 cysteine residues on the outer sides (excluding Xaa1 in a case where the Xaa1 represents a cysteine residue) are disulfide-bonded. Alternatively, in the peptide of the formula I, the sulfide groups of the 2 cysteine residues on the outer sides may be linked via a linker represented by the following formula:

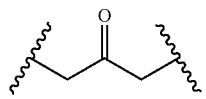 [SMILES: *CC(=O)C*]

In the above formula, the broken line parts each mean a binding part to which the sulfide group binds. The linker is more stable against the reduction reaction or the like than the ordinary disulfide bond. Accordingly, the linker is preferably used, for example, when a radioactive metal nuclide such as zirconium that may destabilize the disulfide bond is used.

In the amino acid sequence of the IgG-binding peptide of the above formula (I), the 1st and 2nd amino acid residues Xs, and the 16th and 17th amino acid residues Xs counted from the N terminus in the case of 17 amino acid residues may be deleted, and such a peptide is 13 amino acids in length.

The expression "in the case of 17 amino acid residues" as used in the present specification is an expression for convenience, which numbers the amino acid residues from 1st to 17th in order from the N terminus of the 17 residues that are the longest amino acids in length of the IgG-binding peptide of the formula (I), so that the amino acid residues of the peptide can be each referred to as an amino acid number.

Further, it is preferred that the amino acid residues other than cysteine (C) in the amino acid sequence of the peptide of the above formula (I), that is, the 1st to 3rd, 5th, 6th, and 15th to 17th amino acid residues counted from the N terminus in the case of 17 amino acid residues, are respectively selected from the following ones. Herein, each capital alphabet represents a single-letter expression of an amino acid:

1st amino acid residue=S, G, F, R, or none;
2nd amino acid residue=D, G, A, S, P, homocysteine, or none;
3rd amino acid residue=S, D, T, N, E, or R;
5th amino acid residue=A or T;
6th amino acid residue=Y or W;
15th amino acid residue=S, T or D;
16th amino acid residue=H, G, Y, T, N, D, F, homocysteine, or none; and
17th amino acid residue=Y, F, H, M, or none.

Preferred specific examples of the IgG-binding peptide of the formula (I) include
1) DCAYH(Xaa1)GELVWCT (SEQ ID NO: 1),
2) GPDCAYH(Xaa1)GELVWCTFH (SEQ ID NO: 2),
13) RGNCAYH(Xaa1)GQLVWCTYH (SEQ ID NO: 3), and
14) G (Xaa2) DCAYH (Xaa1) GELVWCT (Xaa2) H (SEQ ID NO: 4), and
particularly preferred example includes 2) GPDCAYH(Xaa1)GELVWCTFH (SEQ ID NO: 2) (in the formula, Xaa1 represents a lysine residue, and Xaa2 represents homocysteine, and preferably both cysteines and/or both homocysteines form a disulfide bond with each other).

As described above, the IgG-binding peptide of the above formula (I) involved in the present invention is characterized in that the IgG-binding peptide has at least 2 cysteine (C) residues that are separated from each other in each amino acid sequence, and the cysteine residues are arranged so as to form a disulfide bond between the cysteine residues, and in the preferred peptide, 2 cysteine residues are disulfide-bonded to form a cyclic peptide, and arbitrary 1 to 3 amino acid residues other than cysteine may be contained on the N-terminal side and the C-terminal side of the respective cysteine residues. In a case where 1 to 3 amino acid residues are contained on the N-terminal side and the C-terminal side of the respective cysteine residues, each of the 1st to 2nd and 16th to 17th amino acid residues counted from the N terminus in the case of 17 amino acid residues is the one as described above.

As described above, in the IgG-binding peptide to be used in the present invention, Xaa1 represents a protein constituent amino acid such as a lysine residue, a cysteine residue, an aspartic acid residue, or a glutamic acid residue, or a non-protein constituent amino acid such as diaminopropionic acid, or 2-aminosuberic acid, and preferably a lysine residue. It is preferred that Xaa1 is modifiable with a crosslinking agent described later. In the present specification, the expression "non-protein constituent amino acid" refers to an amino acid that is not used to form a protein in a living body. In order to enhance the site specificity in modifying the IgG-binding peptide to be used in the present invention with a crosslinking agent, it is preferred that the IgG-binding peptide to be used in the present invention has no or little (for example, only one or two) residues that are the same as Xaa1 in the sequence. For example, in a case where the Xaa1 is a lysine residue, it is preferred that the IgG-binding peptide to be used in the present invention has no or little lysine residues at sites other than the site of Xaa1 in the sequence.

The IgG-binding peptide to be used in the present invention has around 10 or more times, preferably around 50 or more times, and more preferably around 200 or more times higher binding affinity for human IgG as compared with other human immunoglobulins (IgA, IgE, and IgM). The dissociation constant (Kd) as to the binding of the IgG-binding peptide to be used in the present invention to human IgG can be determined by surface plasmon resonance spectrum analysis (using, for example, a BIACORE system), and is, for example, $1 \times 10^{-1}$ M to less than $1 \times 10^{-3}$ M, preferably less than $1 \times 10^{-4}$ M, and more preferably less than $1 \times 10^{-5}$ M.

The IgG-binding peptide to be used in the present invention binds to the Fc domain of an IgG antibody. As shown in Examples of WO 2017/217347, the IgG-binding peptide to be used in the present invention comes in close contact at the above Xaa1 with a specific region of the IgG Fc, that is, in accordance with the Eu numbering in human IgG Fc, the Lys248 residue (hereinafter, simply referred to as "Lys248" in the present specification, and which corresponds to the 18th residue of human IgG CH$_2$ (SEQ ID NO: 5)), or the Lys246 residue (hereinafter, simply referred to as "Lys246" in the present specification, and which corresponds to the 16th residue of human IgG CH$_2$ (SEQ ID NO: 5)), and preferably Lys248.

The IgG-binding peptide to be used in the present invention can be obtained by a method disclosed in, for example, WO 2017/217347. Specifically, the IgG-binding peptide can be produced by, for example, a peptide synthesis method such as a conventional liquid phase synthesis method or solid phase synthesis method, or peptide synthesis by an automatic peptide synthesizer (Kelley et al., Genetics Engineering Principles and Methods, Setlow, J. K. eds., Plenum Press NY. (1990) Vol. 12, pp. 1-19; Stewart et al., Solid-Phase Peptide Synthesis (1989) W.H. Freeman Co.; Houghten, Proc. Natl. Acad. Sci. USA (1985) 82: p. 5132; and "New Biochemical Experimental Course 1 Protein IV" (1992) edited by The Japanese Biochemical Society, published by Tokyo Kagaku Dozin). Alternatively, the IgG-binding peptide may be produced by a genetic recombination method, a phage display method, or the like using a nucleic acid encoding the IgG-binding peptide to be used in the present invention. For example, DNA encoding the amino acid sequence of the IgG-binding peptide to be used in the present invention is incorporated into an expression vector, the DNA-incorporated vector is introduced into a host cell, the vector-introduced host cell is then cultured, and thus the desired peptide can be produced. The produced peptide can be recovered or purified by a routine procedure, for example, chromatography such as gel filtration chromatography, ion-exchange column chromatography, affinity chromatography, reverse-phase column chromatography, or high-performance liquid chromatography (HPLC), ammonium sulfate fractionation, ultrafiltration, immune adsorption, or the like.

In the peptide synthesis, for example, amino acids (regardless of being natural or non-natural) which are protected at functional groups other than the α-amino and α-carboxyl groups for bonding are prepared, and the peptide bond formation reaction is performed between the α-amino group of one amino acid and the α-carboxyl group of another amino acid. In general, the carboxyl group of an amino acid residue positioned at the C terminus of the peptide is bound in advance onto a solid phase via an appropriate spacer or linker. The protective group at the amino terminus of the dipeptide thus obtained is selectively removed, and the formation of a peptide bond with the α-carboxyl group of a subsequent amino acid is performed. The operation as described above is continuously performed to produce a peptide having protected side groups. In the end, all of the protective groups are removed, and the peptide is separated from the solid phase. The details of the type of the protective group, the protection method, and the peptide binding method are disclosed in the literatures described above.

The production by the genetic recombination method can be performed by, for example, a method including inserting DNA encoding the peptide of the present invention into an appropriate expression vector, introducing the vector to an appropriate host cell, culturing the cell, and recovering the desired peptide from the inside of the cell or the extracellular fluid. The vector is not limited, and is, for example, a vector such as a plasmid, a phage, a cosmid, a phagemid, or a virus. Examples of the plasmid vector include, but are not limited to, a plasmid derived from *E. coli* (for example, pET22b(+), pBR322, pBR325, pUC118, pUC119, pUC18, pUC19, pBluescript, or the like), a plasmid derived from *Bacillus subtilis* (for example, pUB110, pTP5, or the like), and a plasmid derived from yeast (for example, YEp13, YCp50, or the like). Examples of the phage vector include, but are not limited to, a T7 phage display vector (T7Select10-3b, T7Select1-1b, T7Select1-2a, T7Select1-2b, T7Select1-2c, or the like (Novagen)), and a λ phage vector (Charon4A, Charon21A, EMBL3, EMBL4, λgt10, λgt11, λZAP, λZAPII, or the like). Examples of the virus vector include, but are not limited to, an animal virus such as a retrovirus, an adenovirus, an adeno-associated virus, a vaccinia virus, or a hemagglutinating virus of Japan, and an insect virus such as a baculovirus. Examples of the cosmid vector include, but are not limited to, Lorist 6, Charomid 9-20, and Charomid 9-42. As non-limiting examples of the phagemid vector, pSKAN, pBluescript, pBK, or pComb3H is known. The vector may contain a regulatory sequence that allows the desired DNA to be expressed, a selective marker for selection of a vector containing the desired DNA, a multi-cloning site for insertion of the desired DNA, and the like. As such a regulatory sequence, a promoter, an enhancer, a terminator, a Shine-Dalgarno (S-D) sequence or ribosome binding site, a replication origin, a poly(A) site, and the like are included. Further, as the selective marker, for example, an ampicillin resistance gene, a neomycin resistance gene, a kanamycin resistance gene, a dihydrofolate reductase gene, or the like may be used. The host cell to which the vector is introduced is a bacterium such as *E. coli*, or *Bacillus subtilis*, a yeast cell, an insect cell, an animal cell (for example, a mammalian cell), a plant cell, or the like. The transformation or transfection of such a cell is performed by, for example, a calcium phosphate method, an electroporation method, a lipofection method, a particle gun method, a polyethylene glycol (PEG) method, or the like. The culture of the transformed cell is performed in accordance with a method usually used in the culture of a host organism. For example, a culture solution for a microorganism such as *E. coli* or a yeast cell contains a carbon source, a nitrogen source, inorganic salts, and the like, which can be assimilated by a host microorganism. In order to facilitate the recovery of the IgG-binding peptide to be used in the present invention, it is preferred that the peptide generated by the expression is extracellularly secreted. This can be performed by binding DNA encoding a peptide sequence that allows peptide secretion from the cell, onto the 5'-terminal side of DNA encoding the desired peptide. The fusion peptide transferred to the cell membrane is cleaved by signal peptidase, so that the desired peptide is secreted and released into a medium. Alternatively, the desired peptide accumulated in the cell can also be recovered. In this case, the cell is physically or chemically destroyed, and the desired peptide is recovered by using a protein purification technique.

Therefore, the present invention also relates to a nucleic acid encoding a peptide to be used in the present invention. In this regard, the nucleic acid includes DNA or RNA (for example, mRNA).

In a case where the IgG-binding peptide to be used in the present invention is fused with another protein, the IgG-binding peptide and another protein are separately prepared, and then the IgG-binding peptide and the protein may be fused with each other by using a linker as needed, or may be prepared by a genetic recombination method as a fusion protein with the addition of an appropriate linker as needed. In this case, it is preferred to prepare the fusion protein without impairing the binding activity of the IgG-binding peptide of the present invention to IgG.

It is preferred that the IgG-binding peptide to be used in the present invention is modified by a crosslinking agent. As described above, the IgG-binding peptide to be used in the present invention comes in close contact at the above Xaa1 with a specific region of the IgG Fc, that is, Lys248 or Lys246, and preferably Lys248 in accordance with the Eu numbering in human IgG Fc, as shown in Examples described later. Accordingly, by modifying the Xaa1 of the IgG-binding peptide to be used in the present invention with a crosslinking agent, and subjecting the peptide to crosslinking reaction with IgG, a crosslinking structure can be site-specifically formed between the Xaa1 of the IgG-binding peptide and Lys248 or Lys246, preferably Lys248 of IgG Fc. As described above, by modifying the Xaa1 of the IgG-binding peptide to be used in the present invention with a crosslinking agent and various compounds, and subjecting the peptide to crosslinking reaction with IgG, various compounds can be introduced specifically and easily to IgG. Further, according to the present invention, since a compound of the above formula (I) and other compounds can be introduced to IgG via the IgG-binding peptide, compounds having various structures can be introduced to IgG. In addition, in the present invention, the yield of the product to be obtained is high and the modification of antibody itself is not involved, and therefore, the present invention also has an advantage that the possibility of reducing the antibody function is low.

The IgG-binding peptide to be used in the present invention can also be used for IgG of an animal other than human, preferably of a mammal. In this case, a site in the IgG, to which the IgG-binding peptide to be used in the present invention binds, can be easily specified by a person skilled in the art who have read the present specification, for example, by aligning the sequence of human IgG with the sequence of IgG of another animal.

In the present invention, the "crosslinking agent" is a chemical substance for linking the IgG-binding peptide to be used in the present invention to IgG Fc by a covalent bond. The crosslinking agent of the present invention can be appropriately selected by a person skilled in the art, and can be a compound having at least two sites to which desired amino acids (for example, a lysine residue, a cysteine residue, an aspartic acid residue, a glutamic acid residue, 2-aminosuberic acid, diaminopropionic acid, arginine, or the like) can bind. Examples of the crosslinking agent include, but are not limited to, a crosslinking agent containing preferably two or more succinimidyl groups, such as disuccinimidyl glutarate (DSG), or disuccinimidyl suberate (DSS), a crosslinking agent containing preferably two or more imidic acid moieties, such as dimethyl adipimidate dihydrochloride (DMA), dimethyl pimelimidate dihydrochloride (DMP), or dimethyl suberimidate dihydrochloride (DMS), and a crosslinking agent having a SS bond, such as dimethyl 3,3'-dithiobispropionimidate dihydrochloride (DTBP), or dithiobis (succinimidyl propionate) (DSP).

The IgG-binding peptide modified by the crosslinking agent of the present invention can be produced by a method disclosed in WO 2017/217437.

Further, the IgG-binding peptide to be used in the present invention may be modified by C-terminal amidation or the like in order to improve the stability and the like of the IgG-binding peptide.

In the IgG-binding peptide to be used in the present invention, a modification linker is introduced in the N terminus. As the modification linker, for example, one represented by the above formula (III) can be mentioned.

The number of molecules of polyethylene glycol (PEG) of the PEG linker of $L_1$ is not particularly limited, and can be set to, for example, 1 to 50 molecules, 1 to 20 molecules, 2 to 10 molecules, or 2 to 6 molecules.

$L_2$ represents an amino acid sequence consisting of 0 to 5 or less amino acid residues, and it is preferred that the $L_2$ contains at least cysteine.

$L_3$ may be a group containing at least a dibenzocyclooctyne (DBCO) group, and one formed by binding commercially available various DBCO reagents (for example, DBCO-C6-Acid, Dibenzylcyclooctyne-Amine, Dibenzylcyclooctyne-Maleimide, DBCO-PEG acid, DBCO-PEG-NHS ester, DBCO-PEG-Alcohol, DBCO-PEG-amine, DBCO-PEG-NH-Boc, Carboxyrhodamine-PEG-DBCO, Sulforhodamine-PEG-DBCO, TAMRA-PEG-DBCO, DBCO-PEG-Biotin, DBCO-PEG-DBCO, DBCO-PEG-Maleimide, TCO-PEG-DBCO, DBCO-mPEG, and the like) to $L_1$ or $L_2$ can be selected. As an example, one formed by reacting the DBCO-maleimide represented by the above formula (IV) with a cysteine residue of $L_2$ can be mentioned.

The modification linker of the formula (III) is provided with DBCO that serves as a substrate for a click reaction, and therefore can be bound by a click reaction to a ligand provided with an azido group. The click reaction can be performed under the known conditions, and it is preferred to maintain the click reaction at a temperature of 25 to 50° C. for 20 to 40 minutes in a reaction solvent. As the reaction solvent, in addition to a buffer solution such as a phosphate buffer solution, a Tris buffer solution, an acetate buffer solution, or a citrate buffer solution, a mixed solvent in which a small amount of an organic solvent such as dimethyl sulfoxide has been mixed with a buffer solution can be used.

<IgG Antibody>

In one aspect, the present invention relates to an IgG antibody to which the modified IgG-binding peptide according to the present invention is bound. The IgG antibody can be formed by mixing a modified IgG-binding peptide with an IgG antibody, and generating a crosslinking reaction between the modified IgG-binding peptide and the IgG. In the crosslinking reaction, preferably an amino acid residue of the Xaa1 of the IgG-binding peptide represented by the above formula (I), and Lys248 or Lys246, preferably Lys248 of IgG Fc can be site-specifically generated. This crosslinking reaction can be performed by a method disclosed in WO 2017/217437.

The IgG antibody to which the present invention is applied is not particularly limited as long as it contains at least one heavy chain. The heavy chain has a molecular weight of around 50 kDa, and contains at least an antigen-binding domain and a Fc region. To the heavy chain, a light chain having a molecular weight of around 25 kDa may be bound via a disulfide bond. The molecular weight of the IgG antibody according to the present invention is not particularly limited as long as it satisfies the above constitution, and is preferably around 100 to 170 kDa, and more preferably around 120 to 170 kDa.

The term "around" in the present invention is referred to as a numerical range of ±10%.

Since the IgG antibody according to the present invention is formed by a crosslinking reaction that is site-specific to a Fc region, the possibility that the crosslinking reaction negatively affects the activity of IgG is low. Further, by linking the modified IgG-binding peptide to IgG, new functionality can be added to the IgG. As the IgG, various antibody medicines can be used.

<Ligand>

In another aspect of the present invention, a peptide-based ligand represented by the above formula (II) is provided.

The compound of the above formula (II) can bind to a polypeptide such as an IgG-binding peptide, a modified IgG-binding peptide, an IgG antibody, or an antibody fragment, or a target molecular element such as a ligand binding to another target molecule, via a group represented by $NR^1R^2$ at the terminus of the side chain of lysine, and therefore, the compound can be used for radioactive metal labeling of various kinds of target molecular elements. Further, since the compound of the above formula (II) includes a peptide chain having a phenylalanine residue and a lysine residue as the main chain and the main chain is metabolized in the liver, the accumulation of a radioactive metal in the liver is suppressed, and the excretion in urine is promoted, and thus the compound is excellent in pharmacokinetics. As a result, the compound can be applied to a radiotherapeutic agent using not only a short-half-life radioactive metal nuclide but also a radioactive metal nuclide that emits cytotoxic α-rays and β-rays, and since the radioactivity that becomes the background of the abdomen in radioactive image diagnosis is a low level, the detection/diagnosis of a lesion site of the abdomen becomes easy.

In a case where $R^1$ and $R^2$ are bound and form a maleimide group together with the nitrogen atom in the above formula (II), the binding to a SH group of cysteine can be performed, and in a case where one of $R^1$ and $R^2$ is a hydrogen atom and the other is a group represented by $CO(CH_2)_4N_3$, the binding to an alkyne such as DBCO can be performed by a click reaction. Accordingly, with the use of the modification linker represented by the above formula (III), and further, a compound represented by the following formula (II-2) as a ligand, a ligand represented by the following formula (II-2) can be bound to the modified IgG-binding peptide or an IgG antibody to which the modified IgG-binding peptide has been bound.

a citrate buffer solution, a mixed solvent in which a small amount of an organic solvent such as dimethyl sulfoxide has been mixed with a buffer solution can be used.

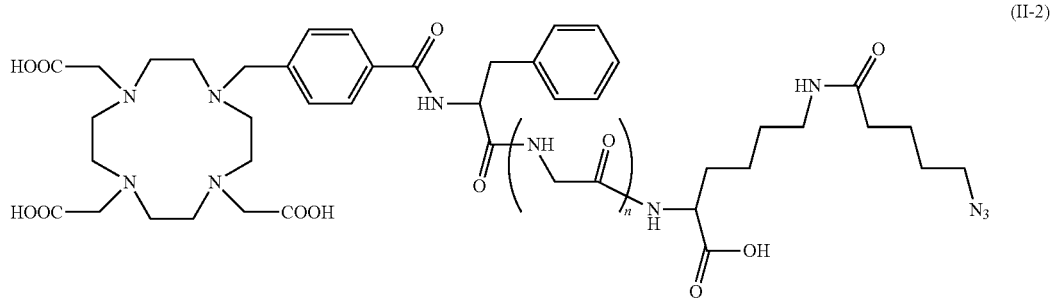

(II-2)

In the formula (II-2), n is 0 or 1.

The ligand of the present invention may form a pharmacologically acceptable salt. Examples of the salt include an acid addition salt, and a base addition salt.

The acid addition salt may be either an inorganic acid salt, or an organic acid salt.

Examples of the inorganic acid salt include a hydrochloride, a hydrobromide, a sulfate, a hydroiodide, a nitrate, and a phosphate.

Examples of the organic acid salt include a citrate, an oxalate, an acetate, a formate, a propionate, a benzoate, a trifluoroacetate, a maleate, a tartrate, a methanesulfonate, a benzenesulfonate, and a p-toluenesulfonate.

The base addition salt may be either an inorganic base salt, or an organic base salt.

Examples of the inorganic base salt include a sodium salt, a potassium salt, a calcium salt, a magnesium salt, and an ammonium salt.

Examples of the organic base salt include a triethylammonium salt, a triethanolammonium salt, a pyridinium salt, and a diisopropylammonium salt.

<Modified Antibody>

In another aspect of the present invention, a modified antibody containing an IgG antibody and an IgG-binding peptide bound to the IgG antibody, in which the IgG-binding peptide has an amino acid sequence represented by the above formula (I) which comprises of 13 to 17 amino acid residues, and a compound represented by the above formula (II-1) is linked at a position of the lysine residue via a modification linker to the N terminus of the IgG-binding peptide, is provided.

In the modified antibody of the present invention, it is preferred that a binding site between the modification linker and the lysine residue of the compound represented by the above formula (II-1) is formed by a click reaction between a DBCO group and an azido group. More preferably, one in which an alkyl azide group having 1 to 10 carbon atoms has been introduced to the lysine residue of the compound represented by the above formula (II-1) can be used, and furthermore preferably the compound represented by the above formula (II-2) is used. Further, in this case, it is preferred that the modification linker is represented by the above formula (III). The click reaction can be performed under the known conditions, and it is preferred to maintain the click reaction at a temperature of 25 to 50° C. for 20 to 40 minutes in a reaction solvent. As the reaction solvent, in addition to a buffer solution such as a phosphate buffer solution, a Tris buffer solution, an acetate buffer solution, or <Radioactive Metal-Labeled Antibody>

In another aspect of the present invention, a radioactive metal-labeled antibody in which a radioactive metal has been coordinated to the above modified antibody is provided.

Examples of the radioactive metal nuclide include $^{111}$In (indium), $^{89}$Zr (zirconium), $^{67/68}$Ga (gallium), $^{64}$Cu (copper), $^{90}$Y (yttrium), $^{213}$Bi (bismuth), $^{225}$Ac (actinium), and $^{177}$Lu (lutetium). The radioactive metal nuclide to be bound to an IgG-binding peptide can be selected depending on the application of the radioactive metal-labeled antibody of the present invention. For example, $^{111}$In, $^{89}$Zr, $^{64}$Cu, and $^{67/68}$Ga can be used for detection/diagnosis of cancer, and for example, $^{89}$Zr and $^{64}$Cu can be used for PET, and $^{111}$In can be used for SPECT. For therapeutic purposes, $^{225}$Ac and $^{177}$Lu can be used.

In order to coordinate a radioactive metal to the modified antibody of the present invention, for example, both may be maintained at a temperature of 25 to 120° C. for 30 to 180 minutes in a reaction solvent. As the reaction solvent, a phosphate buffer solution, a Tris buffer solution, an acetate buffer solution, a citrate buffer solution, a HEPES buffer solution, or the like can be used.

<Radiopharmaceutical>

In another aspect of the present invention, a radiopharmaceutical containing the above radioactive metal-labeled antibody is provided.

The radiopharmaceutical according to the present invention can be used, for example, as a nuclear medicine diagnostic imaging agent, or a diagnostic agent for cancer. In this case, the IgG antibody can be appropriately selected depending on the kind of cancer, and for example, trastuzumab can be used if the cancer is breast cancer, and cetuximab can be used if the cancer is colon cancer. The nuclear medicine diagnostic imaging agent or the diagnostic agent for cancer can be formulated in accordance with a conventional method (for example, see Remington's Pharmaceutical Science, latest edition, Mark Publishing Company, Easton, USA).

EXAMPLES

Hereinafter, the present invention is further specifically described by way of Examples, however, the present invention is not limited to the contents of these Examples.

Example 1: Preparation of DBCO-Containing IgG Antibody

An IgG antibody to which a DBCO-modified IgG-binding peptide was bound was prepared, which is shown below.

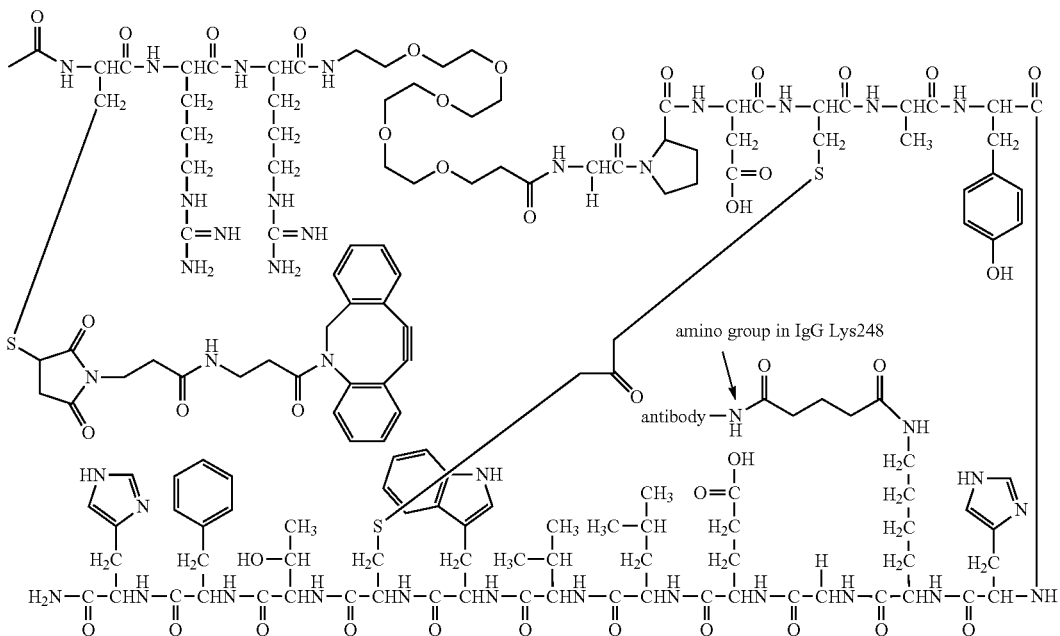

1) Preparation of DBCO-Modified IgG-Binding Peptide

An amino PEGS-added IgG-binding peptide GPD-CAYHKGELVWCTFH (SEQ ID NO: 2) in which the amino group at the N terminus was modified with an acetyl group (SEQ ID NO: 2, in which two Cys residues in the molecule were crosslinked with dichloroacetone, and the C terminus was amidated) was synthesized by a 9-fluorenylmethoxy-carbonyl (Fmoc) solid phase synthesis method in accordance with a conventional method. After the deprotection, 9.1 mg of the purified IgG-binding peptide was dissolved in 100 μL of 0.5% pyridine-containing DMSO (33.3 mM), and supplemented with 50 μL (1.5 times amount in terms of molar ratio relative to the peptide) of 0.5% pyridine-containing DMSO that contained 100 mM DBCO-maleimide, and the resultant mixture was allowed to react at room temperature for 30 minutes. Next, into this peptide solution, 200 μL of DSG (500 mM) dissolved in acetonitrile (final concentration: 286 mM, 30 times molar equivalent to the peptide) was added, and the resultant mixture was allowed to react at 50° C. for 3 hours. The whole amount (350 μL) was divided into two portions, the two portions were each diluted in 5 mL of 10% acetonitrile containing 0.1% TFA, and the supernatant after centrifugation was injected into Inert Sustain (registered trademark) C18 column (7.6 mm, 1×250 mm, GL Science), and eluted with a gradient from the 10% acetonitrile containing 0.1% TFA to 60% acetonitrile containing 0.1% TFA. The eluate was subjected to mass spectrometry, a DBCO-modified IgG-binding peptide as the desired product was recovered, and then the organic solvent was removed, subsequently, the residue was frozen dried.

2) Preparation of DBCO-Containing IgG Antibody 25.2 μL of solution in which the modified IgG-binding peptide prepared in the above 1) had been dissolved in DMSO at a concentration of 4 mM, and 16.8 mL of 20 μM anti-HER2 human antibody (Trastuzumab, Chugai Pharmaceutical Co., Ltd.) dissolved in a 10 mM acetate buffer solution (pH 5.5) were mixed with each other, and the obtained mixture was allowed to react at 37° C. for 3 hours (molar ratio of the peptide to the antibody=3:1). The DBCO-containing antibody prepared in this way was purified by gradient elution of 0 to 0.35 M NaCl in a 10 mM acetate buffer solution (pH 5.5) on a cation-exchange column, CIM multus SO3-8 (8 mL, BIA separation). Other than unreacted antibodies, it was confirmed that a monovalent antibody with one peptide and a bivalent antibody with two peptides were formed. Therefore, the peak of the monovalent antibody was collected, and then desalination and concentration were performed by centrifugation at 3000 g on Vivaspin (10000 Da cutoff, GE Healthcare).

Example 2: Synthesis of DO3ABn-Phe-Lys ((CH$_2$)$_4$—N$_3$)—OH

DO3ABn-Phe-Lys ((CH$_2$)$_4$—N$_3$)—OH (a compound of the formula (II-2) in which n is 0) was synthesized by the following scheme (provided that a product in a step (a) is a compound (4b) and a product in a step (b) is a compound (5b)). In this regard, in the analysis by $^1$H-NMR, JEOL ECS-400 spectrometer (JEOL Ltd.) was used, and in the analysis by electrospray ionization mass spectrometry (ESI-MS), HPLC 1200 series-6130 quadrupole LC/MS mass spectrometer (Agilent Technologies, Inc.) was used.

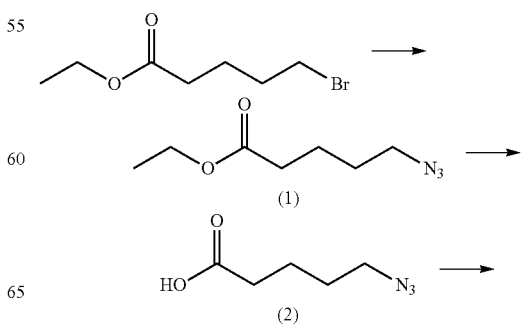

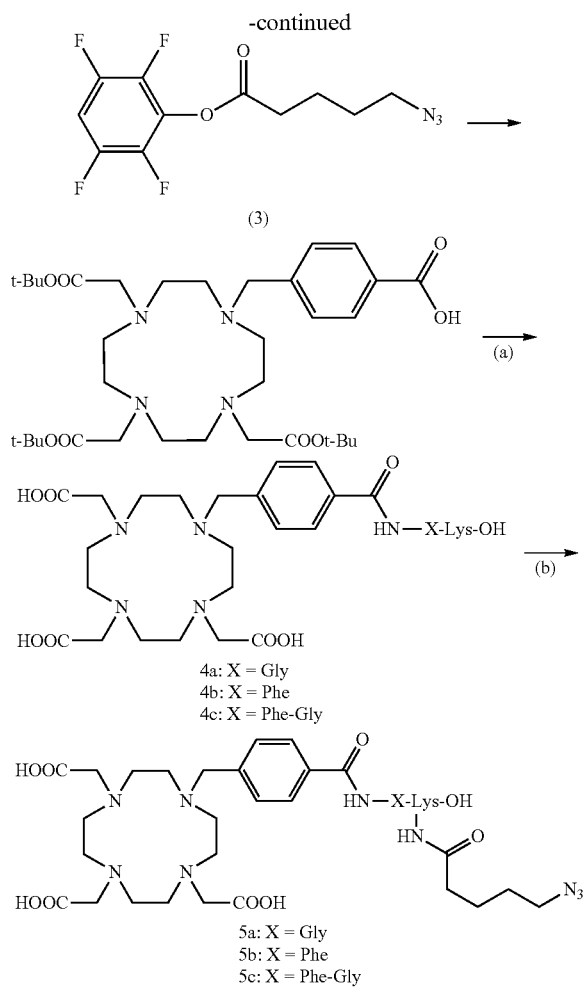

4a: X = Gly
4b: X = Phe
4c: X = Phe-Gly

5a: X = Gly
5b: X = Phe
5c: X = Phe-Gly

Synthesis of ethyl 5-azidovalerate (Compound (1))

Ethyl 5-bromovalerate (1 g, 4.78 mmol) was dissolved in N,N-dimethylformamide (DMF, 3 mL), and into the obtained solution, NaN$_3$ (0.5 g, 7.7 mmol) was added, and the resultant mixture was stirred at 85° C. overnight. The suspension was diluted with water (40 mL), and the diluted suspension was subjected to extraction with diethyl ether (40 mL×3). The obtained solution was concentrated under reduced pressure, and the concentrated solution was used as it was in the following reaction.

Synthesis of 5-azidovaleric acid (Compound (2))

Into the solution of the compound (1), a 1 N NaOH aqueous solution (8.2 mL) was added, and then methanol was added into the obtained mixture until the mixture became homogeneous. The obtained mixture was stirred at room temperature for 4 hours, and then an aqueous solution obtained by concentrating the reaction mixture under reduced pressure was washed with diethyl ether (5 mL). Next, a 5% aqueous solution of citric acid was added to the washed solution to make the solution acidic, and then the acidic solution was subjected to extraction with diethyl ether (5 mL×3). The organic layer was dried with the addition of Na$_2$SO$_4$, and then the solvent was distilled off under reduced pressure to obtain a compound (2) (360 mg, 52.6%).

$^1$H NMR (CDCl$_3$) δ 1.62-1.77 (4H, m, CH$_2$), 2.39-2.43 (2H, t, CH$_2$), 3.29-3.33 (2H, t, CH$_2$)

Synthesis of 2,3,5,6-tetrafluorophenyl 5-azidovalerate (Compound (3))

The compound (2) (17.9 mg, 0.125 μmol), 2,3,5,6-tetrafluorophenol (44.0 mg, 0.250 μmol), and N,N-diisopropylethylamine (DIEA, 53.2 μL, 0.312 μmol) were dissolved in CH$_2$Cl$_2$ (2.0 mL), and then into the obtained solution, 1-ethyl-3-(3-dimethylaminopropyl) carbodiimide hydrochloride (EDC, 48.0 mg, 0.250 μmol) was added while cooling in ice. The solution was returned to room temperature, stirred for 1.5 hours, and then into the resultant solution, ethyl acetate (10 mL) was added, and the obtained mixture was washed with a saturated ammonium chloride solution (3 mL×3). The organic layer was dried with the addition of Na$_2$SO$_4$, and then the solvent was distilled off under reduced pressure to obtain a compound (3) (39.9 mg). The obtained crude product was used as it was in the following reaction although the crude product contained 2,3,5,6-tetrafluorophenol.

Synthesis of DO3ABn-Phe-Lys-OH (Compound (4b))

Phe-Lys was bound to Cl-Trt(2-Cl)-Reisn (product number: A00187, WATANABE CHEMICAL INDUSTRIES, LTD.) by peptide elongation reaction, and to ($^t$Bu)$_3$DO3ABn-COOH (16 to 20 mg), a resin to which 1.3 equivalents of Phe-Lys was bound, O-(7-azabenzotriazole-1-yl)-N,N,N',N'-tetramethyluronium hexafluorophosphate (HATU, 2.5 equivalents), 1-hydroxy-7-azabenzotriazole (HOAt, 2.5 equivalents), and DIEA (5.0 equivalents) were added, and the obtained mixture was stirred at room temperature overnight in DMF (200 μL). The resultant mixture was washed 8 times with DMF, subsequently 4 times with CH$_2$Cl$_2$, and then the resin was dried under reduced pressure. Into the resin after being dried, a mixture of trifluoroacetic acid (TFA)/triisopropylsilane/water=95/2.5/2.5 was added, and the obtained mixture was stirred at room temperature for 3 hours. The solvent was distilled off under reduced pressure, and then the residue was allowed to crystallize with the addition of diethyl ether (5 mL). The crystals were collected by filtration and washed with diethyl ether, and then the washed crystals were dried under reduced pressure to obtain 7.7 mg (25.7%) of a TFA salt of a compound (4b) as white crystals.

Synthesis of DO3ABn-Phe-Lys ((CH$_2$)$_4$—N$_3$)—OH (Compound (5b))

The compound (4b) was dissolved in DMF (0.5 mL), and into the obtained solution, the compound (3) (7.5 equivalents) and DIEA (4.0 equivalents) were added, and the resultant mixture was stirred at room temperature for 3 hours. The solvent was distilled off under reduced pressure, and then the residue was redissolved in water (5 mL). The obtained aqueous solution was washed with CHCl$_3$ (3 mL×3), and then the washed solution was concentrated under reduced pressure, and the concentrated solution was purified by preparative HPLC to obtain 1.7 mg (20.0%) of a TFA salt of a compound (5b) as white crystals. ESI-MS (M+H)$^+$: m/z 881, found: 881

In the purification by preparative HPLC, Imtakt Cadenza C18 (20 mm×150 mm) was used as the column, 0.1% TFA/water was used as the phase A and 0.1% TFA/methanol was used as the phase B, and with a gradient system in which the phase B increased from 10 to 50% in 0 to 45 minutes and from 50 to 100% in 45 to 55 minutes, at a flow rate of 5 mL/min, the peak with a retention time of 38.0 minutes was collected.

Further, in the mass spectrometry, Imtakt US-C18 (4.6 mm×150 mm) was used as the column, 0.1% TFA/water was used as the phase A and 0.1% TFA/acetonitrile was used as the phase B, and with a gradient system in which the phase B increased from 0 to 45% in 0 to 30 minutes and from 45 to 100% in 30 to 40 minutes, at a flow rate of 1 mL/min, the peak with a retention time of 25.0 minutes was analyzed.

Example 3: Synthesis of DO3ABn-Phe-Gly-Lys $((CH_2)_4-N_3)$—OH

DO3ABn-Phe-Lys $((CH_2)_4-N_3)$—OH (a compound of the formula (II-2) in which n is 1) was synthesized by the scheme shown in Example 2 (provided that the product in the step (a) is a compound (4c) and the product in the step (b) is a compound (5c)).

Synthesis of DO3ABn-Phe-Gly-Lys-OH (Compound (4c))

Operation was performed in a similar manner as in the compound (4b) of Example 2 except that a resin to which Phe-Gly-Lys was bound in place of the Phe-Lys was used, and, as a result, 30.0 mg (76.8%) of a TFA salt of a compound (4c) was obtained as white crystals.

Synthesis of DO3ABn-Phe-Gly-Lys $((CH_2)_4-N_3)$—OH (Compound (5c))

Operation was performed in a similar manner as in the compound (5b) of Example 2 except that the compound (4c) was used in place of the compound (4b), and, as a result, 4.6 mg (14.0%) of a TFA salt of a compound (5c) was obtained as white crystals. ESI-MS $(M+H)^+$: m/z 938, found: 938

In the purification by HPLC, as being different from Example 2, Imtakt Cadenza C18 (20 mm×150 mm) was used as the column, 0.1% TFA/water was used as the phase A and 0.1% TFA/acetonitrile was used as the phase B, and with a gradient system in which the phase B increased from 10 to 50% in 0 to 45 minutes and from 50 to 100% in 45 to 55 minutes, at a flow rate of 5 mL/min, the peak with a retention time of 33.9 minutes was collected.

Further, the conditions for mass spectrometry were the same as those in Example 2, but the retention time was 24.7 minutes.

Comparative Example 1: Synthesis of DO3ABn-Gly-Lys $((CH_2)_4-N_3)$—OH

DO3ABn-Gly-Lys $((CH_2)_4-N_3)$—OH (in the formula (II-2), n is 1 and no phenyl residue is present) was synthesized by the scheme shown in Example 2 (provided that the product in the step (a) is a compound (4a) and the product in the step (b) is a compound (5a)).

Synthesis of DO3ABn-Gly-Lys-OH (Compound (4a))

Operation was performed in a similar manner as in the compound (4b) of Example 2 except that a resin to which Gly-Lys was bound in place of the Phe-Lys was used, and, as a result, 8.3 mg (25.3%) of a TFA salt of a compound (4a) was obtained as white crystals.

Synthesis of DO3ABn-Gly-Lys $((CH_2)_4-N_3)$—OH (Compound (5a))

Operation was performed in a similar manner as in the compound (5b) of Example 2 except that the compound (4a) was used in place of the compound (4b), and as a result, 1.5 mg (16.3%) of a TFA salt of a compound (5a) was obtained as white crystals. ESI-MS $(M+H)^+$: m/z 791, found: 791

In this regard, the retention time was 22.6 minutes in the HPLC purification, and the retention time in the mass spectrometry was 19.3 minutes.

Production Example 1: Preparation of DBCO-NGA

By using a technique similar to that disclosed in Journal of Medicinal Chemistry 1997, 40, 2643-2652, a 10 mg/mL NGA solution in which a thiol group was introduced by 2-iminothiolane was prepared. Into 100 μL of this solution, 2 μL of DMSO solution in which 50 equivalents of DBCO-maleimide (purchased from Aldrich) relative to galactose-binding albumin (NGA) had been dissolved was added, and the obtained mixture was allowed to react at 37° C. for 1.5 hours. After completion of the reaction, the solution was purified by a spin column having sephadex G-50 as a carrier and equilibrated with D-PBS(−), to prepare DBCO-NGA to which DBCO was bound in an average number of bound molecules of 2.1.

Production Example 2: Preparation of $^{111}$In-DO3ABn-Phe-Lys-NGA

DO3ABn-Phe-Lys $((CH_2)_4-N_3)$—OH was labeled with $^{111}$In and subjected to a click reaction with DBCO-NGA in accordance with the following scheme (provided that a product in a step (a) is a compound (6b) and a product in a step (b) is a compound (7b)).

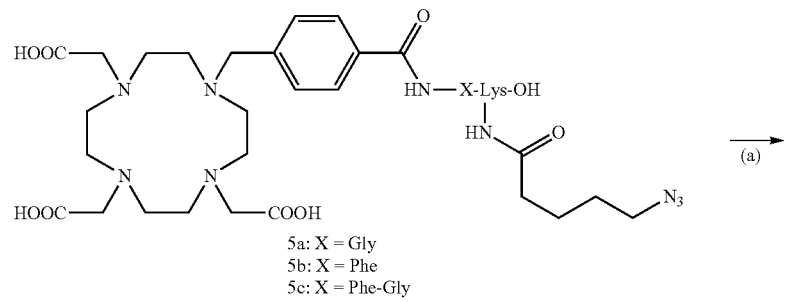

5a: X = Gly
5b: X = Phe
5c: X = Phe-Gly

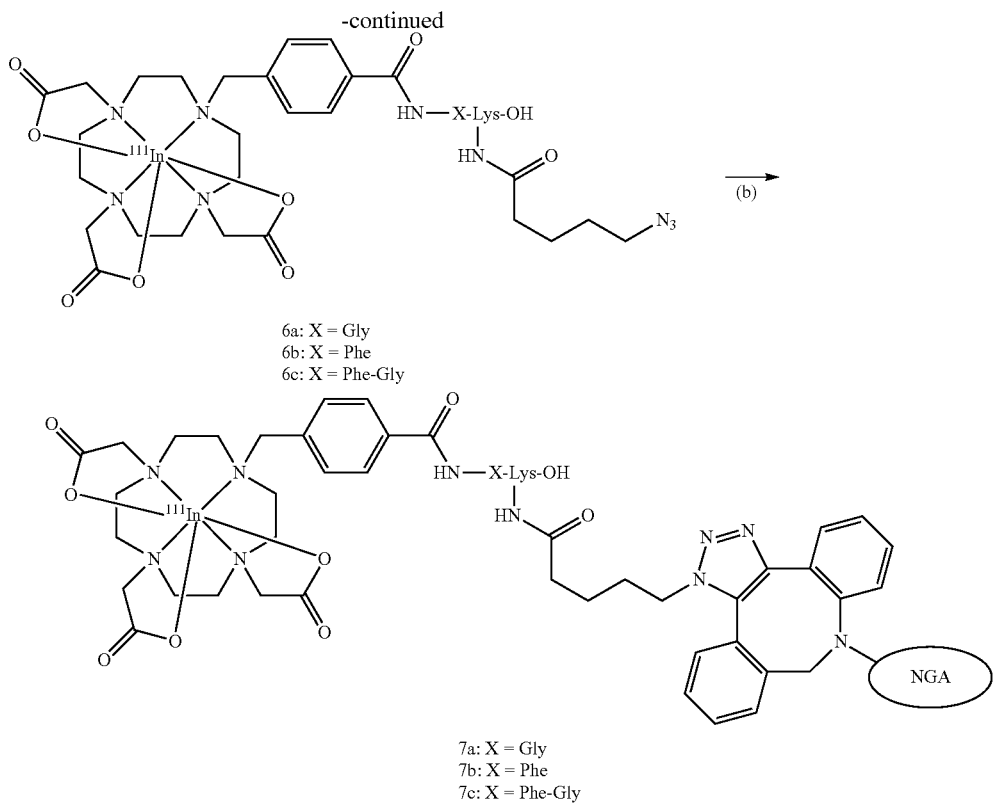

6a: X = Gly
6b: X = Phe
6c: X = Phe-Gly

7a: X = Gly
7b: X = Phe
7c: X = Phe-Gly

Preparation of $^{111}$In-DO3ABn-Phe-Lys ((CH$_2$)$_4$—N$_3$)—OH (Compound (6b))

Into a solution obtained by adding a 1 M acetate buffer solution (pH 5.5, 20 μL) to a $^{111}$InCl$_3$ solution (1.48 MBq/60 μL) and being left to stand at room temperature for 5 minutes, the compound (5b) dissolved in a 0.1 M acetate buffer solution (pH 5.5, 20 μL) at a concentration of 5×10$^{-4}$ M was added. The obtained solution was allowed to react at 95° C. for 5 minutes, and then the resultant was returned to room temperature and supplemented with 10 μL of 0.2 M DTPA solution, and the resultant mixture was left to stand at room temperature for 5 minutes. The reaction mixture was purified by analytical HPLC. Into a solution obtained by subjecting a fraction containing the desired product to solvent replacement with methanol by Sep-pak, 30 μL of D-PBS(-) was added, and the solvent was concentrated under reduced pressure. A 0.05 M acetate buffer solution (pH 5.5) was used as the phase A and methanol was used as the phase B, and with a gradient system in which the phase B increased from 20 to 60% in 0 to 30 minutes and from 60 to 100% in 30 to 35 minutes, at a flow rate of 1 mL/min, the peak with a retention time of 20.2 minutes was collected to perform the purification, and, as a result, a compound (6b) was obtained in a radiochemical yield of >99%.

Preparation of $^{111}$In-DO3ABn-Phe-Lys-NGA (7b)

Into 10 μL of DBCO-NGA solution, 30 μL of D-PBS(-) solution of the compound (6b) was added, and the obtained mixture was allowed to react at room temperature for 14 hours. The solution after the reaction was purified by a spin column having sephadex G-50 as a carrier and equilibrated with D-PBS(-), and, as a result, the desired $^{111}$In-labeled NGA (compound 7 (b)) was obtained in a radiochemical yield of 43.0%.

Production Example 3: Preparation of $^{111}$In-DO3ABn-Phe-Gly-Lys-NGA

DO3ABn-Phe-Gly-Lys ((CH$_2$)$_4$—N$_3$)—OH was labeled with $^{111}$In and subjected to a click reaction with DBCO-NGA in accordance with the scheme shown in Production Example 2 (provided that the product in the step (a) is a compound (6c) and the product in the step (b) is a compound (7c)).

Preparation of $^{111}$In-DO3ABn-Phe-Gly-Lys ((CH$_2$)$_4$—N$_3$)—OH (Compound (6c))

Operation was performed in a similar manner as in the compound (6b) of Production Example 2 except that the compound (5c) was used in place of the compound (5b), and, as a result, a compound (6c) was obtained in a radiochemical yield of 98.7%.

In this regard, the retention time was 18.7 minutes in the HPLC purification.

Preparation of $^{111}$In-DO3ABn-Phe-Gly-Lys-NGA (7c)

Operation was performed in a similar manner as in the compound (6b) of Production Example 2 except that the compound (6c) was used in place of the compound (6b), and, as a result, a compound (7c) was obtained in a radiochemical yield of 50.0%.

Production Example 4: Preparation of $^{111}$In-DO3ABn-Gly-Lys-NGA

DO3ABn-Gly-Lys ((CH$_2$)$_4$—N$_3$)—OH was labeled with $^{111}$In and subjected to a click reaction with DBCO-NGA in accordance with the scheme shown in Production Example 2 (provided that the product in the step (a) is a compound (6a) and the product in the step (b) is a compound (7a)).

Preparation of $^{111}$In-DO3ABn-Gly-Lys ((CH$_2$)$_4$—N$_3$)—OH (Compound (6a))

Operation was performed in a similar manner as in the compound (6b) of Production Example 2 except that the compound (5a) was used in place of the compound (5b), and, as a result, a compound (6a) was obtained in a radiochemical yield of 93.2%.

In the purification by analytical HPLC, Imtakt US-C18 (4.6 mm×150 mm) was used as the column, a 0.05 M acetate buffer solution (pH 5.5) was used as the phase A and methanol was used as the phase B, and with a gradient system in which the phase B increased from 0 to 40% in 0 to 30 minutes and from 40 to 100% in 30 to 35 minutes, at a flow rate of 1 mL/min, the peak with a retention time of 19.1 minutes was collected to perform the purification.

Operation was performed in a similar manner as in the compound (6b) of Production Example 2 except that the compound (6a) was used in place of the compound (6b), and, as a result, a compound (7a) was obtained in a radiochemical yield of 38.0%.

Production Example 5: Preparation of CHX-A"-DTPA-NGA

NGA was dissolved in a 0.1 M borate buffer solution (pH 8.5) to prepare an NGA solution (250 µg/50 µL). Further, p-SCN-CHX-A"-DTPA ((R)-2-amino-3-(4-isothiocyanatophenyl)propyl]-trans-(S,S)-cyclohexane-1,2-diamine-pentaacetic acid, purchased from Aldrich) was dissolved in a 0.1 M borate buffer solution (pH 8.5) (6 mg/mL), and into the obtained solution, 0.1 N NaOH was added to adjust the pH to be 8 to 9, and then the pH-adjusted solution was diluted with a 0.1 M borate buffer solution (pH 8.5) to prepare a p-SCN-CHX-A"DTPA solution (5 mg/mL). Into the NGA solution, 20 equivalents of p-SCN-CHX-A"DTPA solution was added, and the obtained mixture was allowed to react at room temperature overnight.

After completion of the reaction, the solution was purified by a spin column having sephadex G-50 as a carrier and equilibrated with a 0.25 M acetate buffer solution (pH 5.5), and, as a result, the desired CHX-A"DTPA-NGA solution was obtained.

Production Example 6: Preparation of $^{111}$In-CHX-A"-DTPA-NGA

Into a solution obtained by adding a 1 M acetate buffer solution (pH 5.5, 5 µL) to a $^{111}$InCl$_3$ solution (1.48 MBq/20 µL) and being left to stand at room temperature for 5 minutes, the CHX-A"DTPA-NGA solution (30 µg/15 µL) was added. The obtained solution was allowed to react at 37° C. for 1.5 hours, and then the resultant was returned to room temperature and supplemented with 10 µL of 0.2 M DTPA solution, and the resultant mixture was left to stand at room temperature for 5 minutes. The solution after the reaction was purified by a spin column having sephadex G-50 as a carrier and equilibrated with D-PBS(−), and, as a result, the desired $^{111}$In-CHX-A"-DTPA-NGA was obtained.

Example 4: Preparation of Radioactive Metal-Labeled IgG antibody [$^{111}$In] H-FGK-DOTA A click reaction between 1.4 mg (1.5 nmol) of the DBCO-containing IgG antibody obtained in Example 1 and 0.1 mg (75 nmol) of the DO3ABn-Phe-Gly-Lys ((CH$_2$)$_4$—N$_3$)—OH obtained in Example 3 was performed in 167.5 µL of 10 mM acetate buffer solution under a room temperature. After completion of the reaction, the purification was performed by ultrafiltration, and, as a result, a modified antibody in which DOTA-FGK was bound to trastuzumab via a DBCO-modified IgG-binding peptide (hereinafter, referred to as "H-FGK-DOTA") was prepared. The obtained H-FGK-DOTA was mixed with 200 µL of $^{111}$InCl$_3$ solution (19.7 MBq, pH 6.5) in 50 µL of 100 mM HEPES buffer solution. In this regard, the preparation was performed so that the number of moles of the H-FGK-DOTA was 20 to 100 times that of [$^{111}$In]. With the reaction of this mixture at 45° C. for 2 hours, the complex formation reaction was allowed to proceed, and after the complex formation, purification was performed by ultrafiltration. As a result of the measurement of the amount of radioactivity with a radioisotope dose calibrator, the amount of radioactivity of the obtained [$^{111}$In] H-FGK-DOTA was 2.33 MBq, and the radiochemical yield calculated with decay correction was 14.0%.

Further, the [$^{111}$In]H-FGK-DOTA was added dropwise onto filter paper, and then developed with a 100 mM sodium citrate buffer solution. After completion of the development, as a result of the measurement with a TLC scanner (Gita Star, Raytest GmbH), the radiochemical purity was 97.1%.

Example 5: Preparation of Radioactive Metal-Labeled IgG Antibody [$^{111}$In]H-DOTA A click reaction between the DBCO-containing IgG antibody obtained in Example 1 and 0.04 mg (75 nmol) of the 1,4,7,10-tetraazacyclododecane-1,4,7-tris (acetic acid)-10-(azidopropyl ethylacetamide) (Azide-mono-amide-DOTA, Macrocyclics, Inc.) was performed in 167.5 µL of acetate buffer solution under a room temperature. After completion of the reaction, the purification was performed by ultrafiltration, and, as a result, an IgG antibody in which DOTA was bound to trastuzumab via a DBCO-modified IgG-binding peptide (hereinafter, referred to as "H-DOTA") was prepared. By mixing the obtained H-DOTA and 200 µL of 111InCl$_3$ solution (21.3 MBq, pH 6.5) in 50 µL of 100 mM HEPES buffer solution, the complex formation reaction was allowed to proceed, and after the complex formation, the purification was performed by ultrafiltration, and, as a result, [$^{111}$In]H-DOTA 2.99 MBq was obtained. As a result of the calculation of the radiochemical yield and the radiochemical purity, similarly to Example 3, the radiochemical yield was 19.5%, and the radiochemical purity was 99.6%.

Evaluation 1: Animal Experiment (1)

Each of the $^{111}$In-labeled NGA solutions obtained in Production Examples 2 to 4 and 6 was diluted and adjusted with D-PBS(−) so as to have a concentration (11.1 kBq/8 µg protein/100 µL/mouse), and the obtained solution was administered to a 6-week-old male mouse (ddY) via the tail vein. Five mice per group were slaughtered 5 minutes or 1 hour after the administration, the blood and organs of interest were recovered, and after measuring the organ weight, the radioactivity was measured with an auto-well gamma counter.

TABLE 1

|  | Gly-Lys | Phe-Lys | Phe-Gly-Lys | SCN |
| --- | --- | --- | --- | --- |
| Blood | 0.1 ± 0.2 | 0.1 ± 0.0 | 0.1 ± 0.1 | 0.1 ± 0.0 |
| Liver | 89.5 ± 3.4 | 91.1 ± 6.2 | 93.3 ± 3.5 | 95.0 ± 4.1 |
| Spleen | 0.2 ± 0.0 | 0.2 ± 0.0 | 0.2 ± 0.0 | 0.0 ± 0.0 |
| Kidney | 0.1 ± 0.0 | 0.2 ± 0.0 | 0.1 ± 0.0 | 0.1 ± 0.0 |
| Pancreas | 0.0 ± 0.0 | 0.0 ± 0.0 | 0.0 ± 0.0 | 0.0 ± 0.0 |
| Heart | 0.0 ± 0.0 | 0.0 ± 0.0 | 0.0 ± 0.0 | 0.0 ± 0.0 |
| Lung | 0.1 ± 0.1 | 0.1 ± 0.0 | 0.1 ± 0.0 | 0.1 ± 0.0 |
| Stomach | 0.1 ± 0.1 | 0.1 ± 0.1 | 0.0 ± 0.0 | 0.1 ± 0.1 |
| Small intestine | 0.1 ± 0.1 | 0.1 ± 0.1 | 0.1 ± 0.1 | 0.2 ± 0.1 |

TABLE 2

|  | Gly-Lys | Phe-Lys | Phe-Gly-Lys | SCN |
| --- | --- | --- | --- | --- |
| Blood | 0.0 ± 0.0 | 0.3 ± 0.1 | 0.3 ± 0.1 | 0.0 ± 0.0 |
| Liver | 89.1 ± 1.2 | 49.5 ± 5.6 | 47.8 ± 4.0 | 79.9 ± 2.0 |
| Spleen | 0.2 ± 0.0 | 0.2 ± 0.1 | 0.2 ± 0.0 | 0.0 ± 0.0 |
| Kidney | 0.2 ± 0.0 | 0.9 ± 0.3 | 1.1 ± 0.3 | 0.1 ± 0.0 |
| Pancreas | 0.0 ± 0.0 | 0.0 ± 0.1 | 0.0 ± 0.0 | 0.0 ± 0.0 |
| Heart | 0.0 ± 0.0 | 0.0 ± 0.0 | 0.0 ± 0.0 | 0.0 ± 0.0 |
| Lung | 0.0 ± 0.0 | 0.1 ± 0.1 | 0.1 ± 0.0 | 0.0 ± 0.0 |
| Stomach | 0.1 ± 0.1 | 1.1 ± 0.7 | 0.3 ± 0.2 | 0.3 ± 0.3 |
| Small intestine | 2.5 ± 0.7 | 27.8 ± 6.5 | 36.3 ± 3.7 | 8.9 ± 1.2 |

The radioactivity (% ID) of each of the organs 5 minutes after the administration is shown in Table 1. The radioactivity (% ID) of each of the organs 1 hour after the administration is shown in Table 2. The column of Gly-Lys shows the result of the administration of the $^{111}$In-DO3ABn-Gly-Lys-NGA prepared in Production Example 4, the column of Phe-Lys shows the result of the administration of the $^{111}$In-DO3ABn-Phe-Lys-NGA prepared in Production Example 2, the column of Phe-Gly-Lys shows the result of the administration of the $^{111}$In-DO3ABn-Phe-Gly-Lys-NGA prepared in Production Example 3, and SCN shows the result of the administration of the $^{111}$In-CHX-A"-DTPA-NGA prepared in Production Example 6.

As shown in Table 1, the accumulation of radioactivity was observed in the liver 5 minutes after the administration, but the excretion from the liver was observed by incorporating the amino acid sequences of Phe-Lys and Phe-Gly-Lys.

Evaluation 2: Animal Experiment (2)

By using the [$^{111}$In]H-FGK-DOTA obtained in Example 4 and the [$^{111}$In]H-DOTA obtained in Example 5, an in vivo experiment was performed for the purpose of investigating the efficacy of the FGK sequence.

The [$^{111}$In]H-FGK-DOTA and the [$^{111}$In]H-DOTA was each subjected to solvent displacement with phosphate-buffered saline (PBS) and adjusted to 200 kBq per 100 μL, and then administered in an amount of 100 μL to three 6-week old male mice (ddY) via the tail vein under isoflurane anesthesia, and the mice were slaughtered by exsanguination 1, 6, and 24 hours after the administration, respectively. The organs (heart, lung, liver, spleen, kidney, stomach, small intestine, large intestine, bone of lower limb, muscle, and bladder) were removed, and weighed together with blood, urine, feces, and the remaining body, and then the amount of radioactivity was measured. The average value and standard deviation of the radioactivity distribution (% injected dose (ID)) in each time point are shown in FIG. 1. Further, FIG. 2 shows the pharmacokinetics (% ID) of the organs of interest. Statistical analysis was performed by using Student's t-test. In addition, the determination of significant difference was based on P<0.05.

Figure 1B:
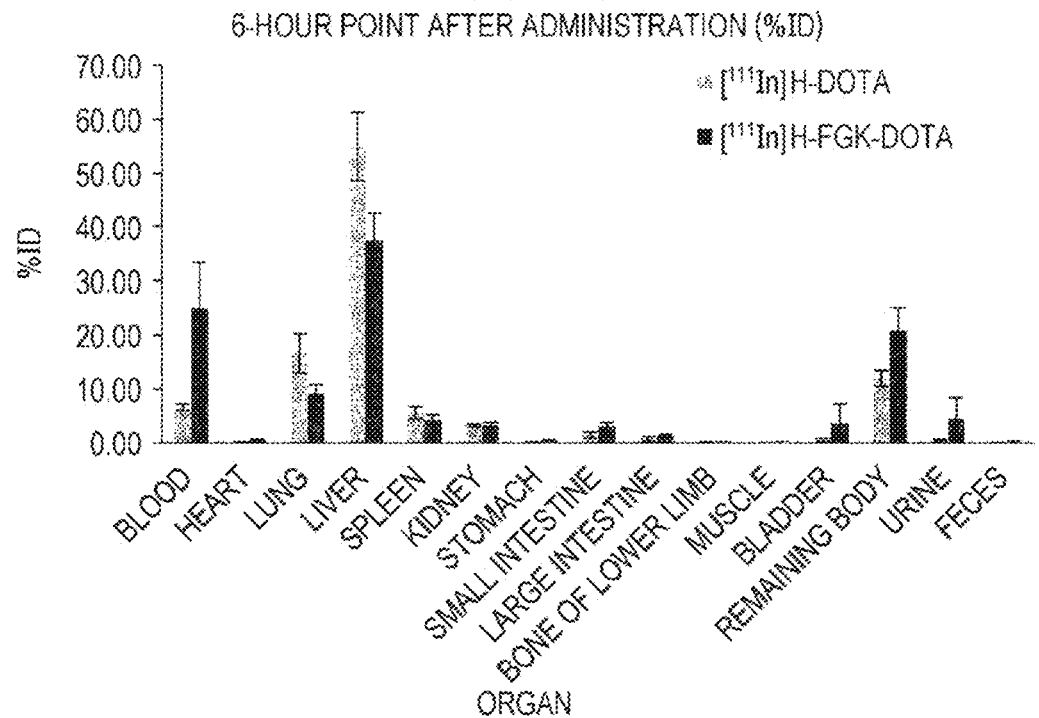
FIG. 1B is a diagram showing an average value and a standard deviation of the radioactivity distribution (% injected dose (ID)) at the 6-hour point after the administration of [$^{111}$In]H-FGK-DOTA and [$^{111}$In]H-DOTA.
Figure 1C:
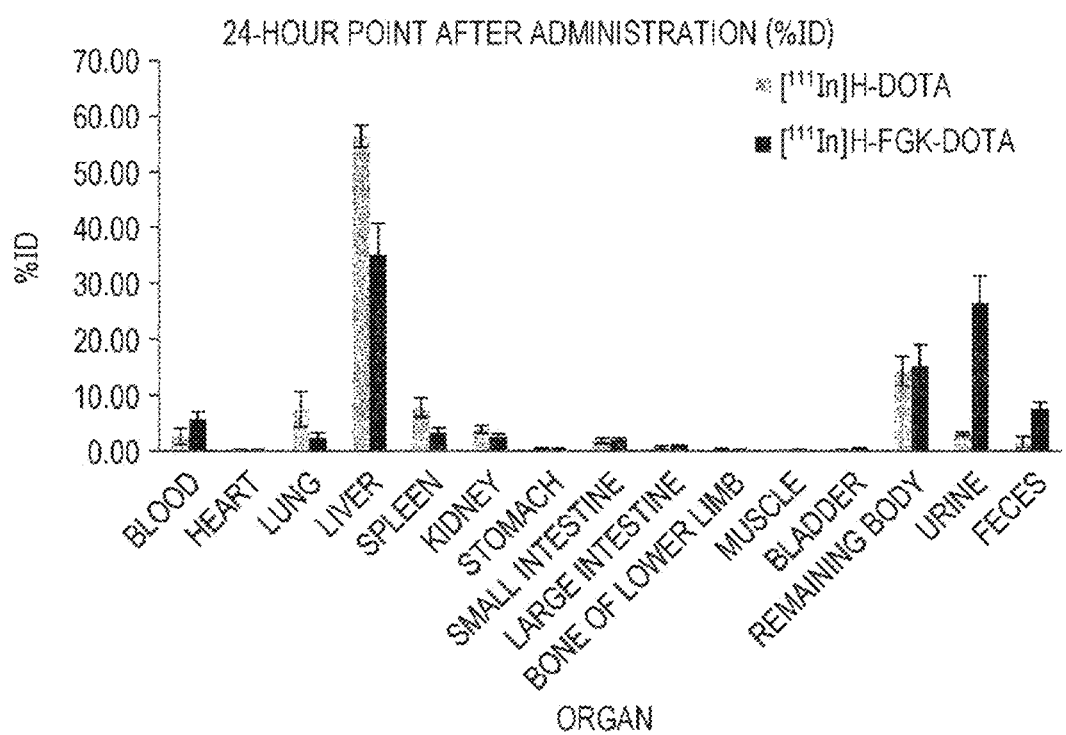
FIG. 1C is a diagram showing an average value and a standard deviation of the radioactivity distribution (% injected dose (ID)) at the 24-hour point after the administration of [$^{111}$In]H-FGK-DOTA and [$^{111}$In]H-DOTA.

FIG. 1A is a diagram showing the results 1 hour after the administration, FIG. 1B is a diagram showing the results 6 hours after the administration, and FIG. 1C is a diagram showing the results 24 hours after the administration.

Figure 2A:
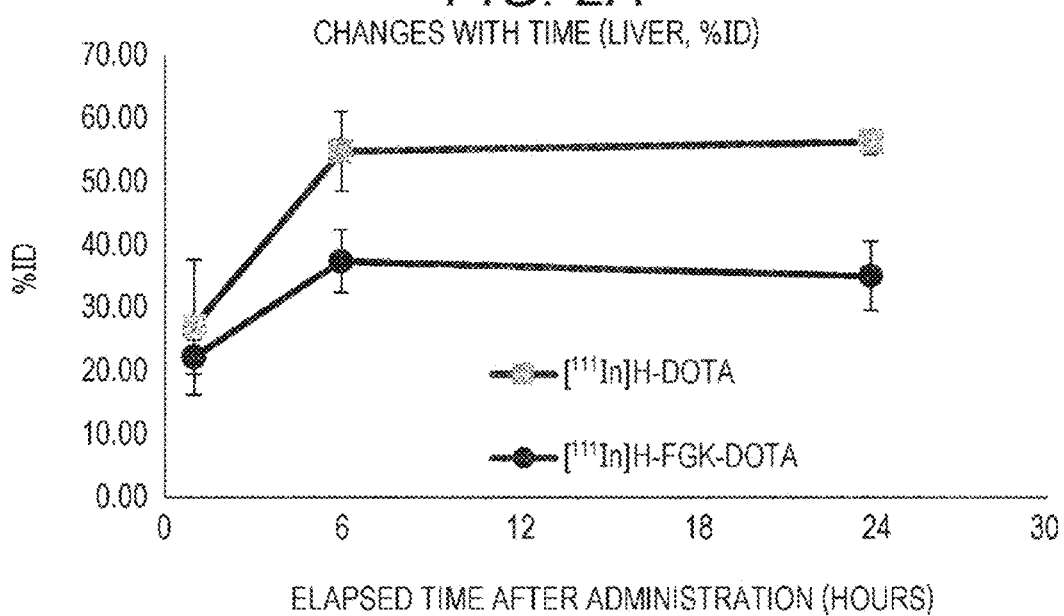
FIG. 2A is a diagram showing changes with time in the radioactivity distribution (% ID) of [$^{111}$In]H-FGK-DOTA and [$^{111}$In]H-DOTA in the liver.
Figure 2B:
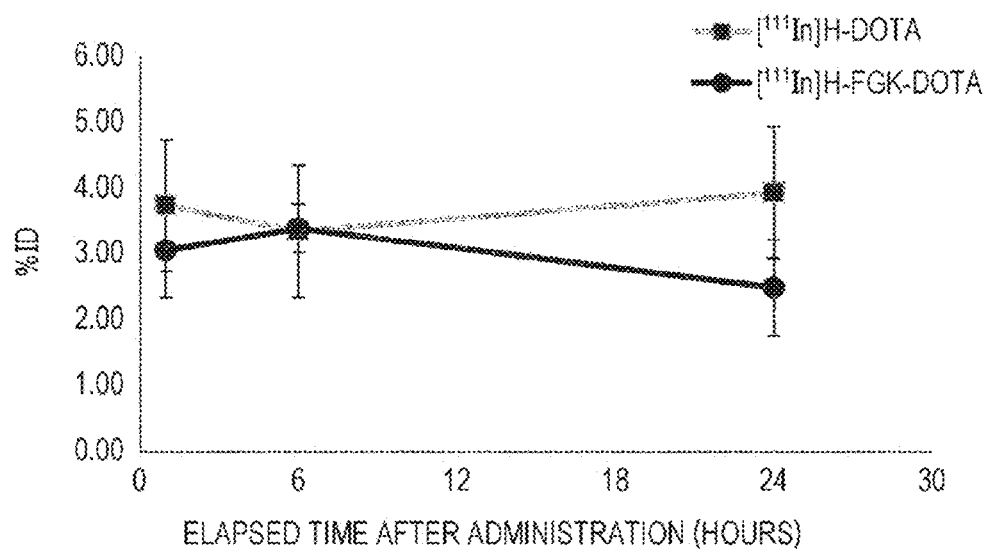
FIG. 2B is a diagram showing changes with time in the radioactivity distribution (% ID) of [$^{111}$In]H-FGK-DOTA and [$^{111}$In]H-DOTA in the kidney.
Figure 2C:
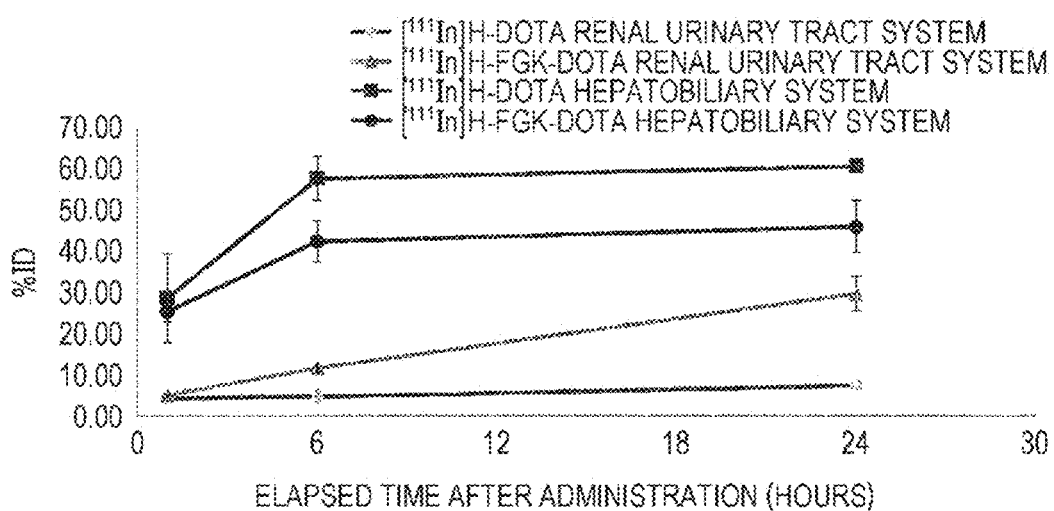
FIG. 2C is a diagram showing changes with time in the radioactivity distribution (% ID) of [$^{111}$In]H-FGK-DOTA and [$^{111}$In]H-DOTA in the excretory system.

FIG. 2A is a diagram showing changes with time in the radioactivity distribution (% ID) in the liver, and FIG. 2B is a diagram showing changes with time in the radioactivity distribution (% ID) in the kidney. In FIG. 2C, the "renal urinary tract system" shows changes with time in the sum of radioactivity distribution (% ID) in the kidney, bladder, and urine, and the "hepatobiliary system" shows changes with time in the sum of radioactivity distribution (% ID) in the liver, small intestine, large intestine, and feces.

From the viewpoints that there was a difference in the uptake into the liver between the [$^{111}$In]H-DOTA and the [$^{111}$In]H-FGK-DOTA at the 6-hour point after the administration and that the excretion in urine of [$^{111}$In]H-FGK-DOTA was significantly increased at the 24-hour point after the administration, it was indicated that the excretion of radionuclides was promoted and the accumulation in the liver was reduced, successfully by the FGK sequence.

The invention claimed is:

1. A modified antibody comprising an IgG antibody, and an IgG-binding peptide bound to the IgG antibody, wherein the IgG-binding peptide comprises an amino acid sequence represented by the following formula (I) which consists of 13 to 17 amino acid residues, and further comprises a compound represented by the following formula (I-1) that is linked at a position of the lysine residue thereof via a modification linker to the N-terminus of the amino acid sequence represented by formula (I), $(X_{1-3})$-C-$(X_2)$-H-(Xaa1)-G-(Xaa2)-L-V-W-C-$(X_{1-3})$(SEQ ID NO: 6), (I)

wherein each X independently represents an amino acid residue other than cysteine, C represents a cysteine residue, H represents a histidine residue, Xaa1 represents a lysine residue, a cysteine residue, an aspartic acid residue, a glutamic acid residue, 2-aminosuberic acid, or diaminopropionic acid, G represents a glycine residue,
Xaa2 represents a glutamic acid residue, a glutamine residue, or an asparagine residue,
L represents a leucine residue,
V represents a valine residue, and
W represents a tryptophan residue, and
the two cysteine residues may be disulfide-bonded or bound to each other via a linker, and the C terminus may be amidated,
and

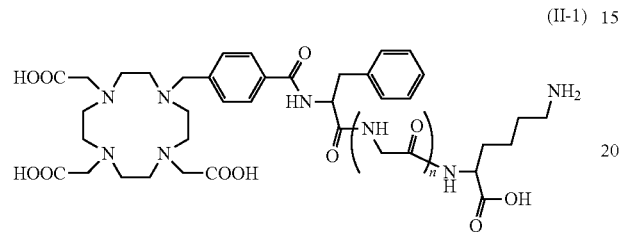

(II-1)

wherein n is 0 or 1.

2. The modified antibody according to claim 1, wherein a binding site between the lysine residue of the compound represented by the above formula (II-1) and the modification linker is formed by a click reaction between a dibenzocyclooctyne (DBCO) group and an azido group.

3. The modified antibody according to claim 2, wherein the modification linker is represented by the following formula (III):

$L_1\text{-}L_2\text{-}L_3$     (III)

wherein
$L_1$ represents a polyethylene glycol linker bound to the N terminus of the amino acid sequence represented by formula (I),
$L_2$ represents an amino acid sequence consisting of 0 or more and 5 or less amino acid residues, and
$L_3$ represents a group having a DBCO group at the terminus,
and wherein
an alkyl azide group having 1 to 10 carbon atoms is introduced to the lysine residue of the compound represented by the above formula (II-1) so that a binding site between the lysine residue and the modification linker is formed by a click reaction.

4. The modified antibody according to claim 1, wherein the IgG-binding peptide represented by the above formula (I) has the following amino acid sequence:

GPDCAYHKGELVWCTFH     (SEQ ID NO: 2)

wherein the two cysteine residues may be disulfide-bonded, and the C terminus may be amidated.

5. The modified antibody according to claim 4, wherein in the above formula (III), $L_2$ represents a cysteine residue, and $L_3$ is formed by reacting DBCO-maleimide represented by the following formula (IV):

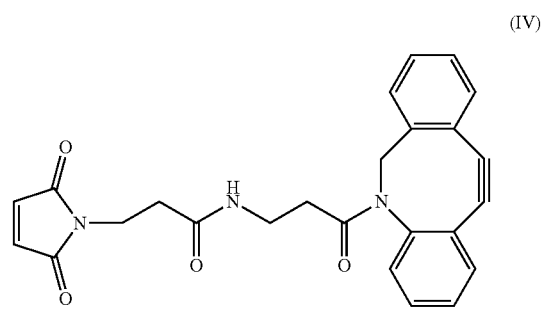 [SMILES: O=C(CCN1C(=O)C=CC1=O)NCCC(=O)N1Cc2ccccc2C#Cc2ccccc21]

(IV)

with the cysteine residue of $L_2$.

6. A radioactive metal-labeled antibody comprising the modified antibody according to claim 1, to which a radioactive metal is coordinated.

7. A radiopharmaceutical comprising the radioactive metal-labeled antibody according to claim 6.

8. A compound comprising a compound represented by the following formula (II), to which a polypeptide to be bound to a target molecule is bound, or a salt thereof:

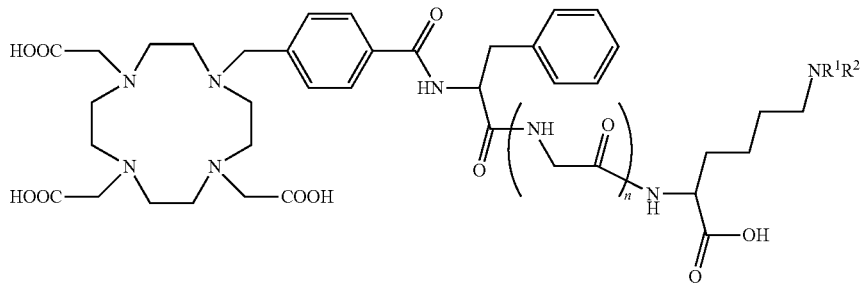

(II)

wherein n is 0 or 1, $R^1$ and $R^2$ both represent a hydrogen atom, or one of $R^1$ and $R^2$ represents a hydrogen atom and the other represents a group represented by $CO(CH_2)_mN_3$ where m is an integer of 1 to 10, or both form a maleimide group or isothiocyanate group together with the nitrogen atom, or a salt thereof.

9. A compound represented by the following formula (II):

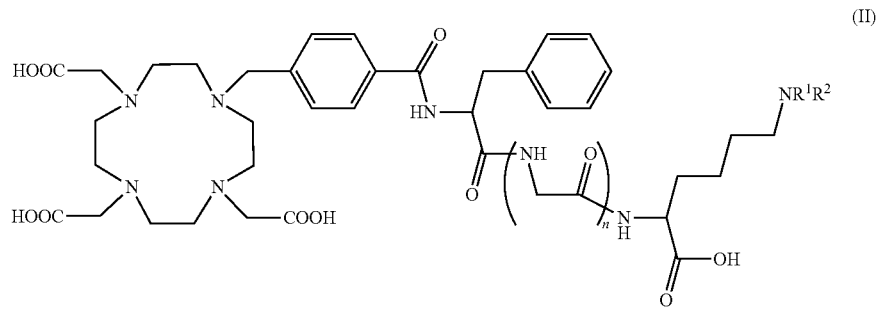

wherein n is 0 or 1, one of R and $R^2$ represents a hydrogen atom and the other represents a group represented by $CO(CH_2)_mN_3$ where m is an integer 1 to 10, to which a polypeptide to be bound to a target molecule is bound, or a salt thereof, wherein
the polypeptide is a modified IgG-binding peptide comprising:
an IgG-binding peptide comprising an amino acid sequence represented by the following formula (I) which consists of 13 to 17 amino acid residues, and
a modification linker represented by the following formula (III) that is bound to the N terminus of the IgG-binding peptide, $(X_{1-3})$-C-$(X_2)$-H-(Xaa1)-G-(Xaa2)-L-V-W-C-$(X_{1})$(SEQ ID NO: 6), wherein
each X independently represents an amino acid residue other than cysteine,
C represents a cysteine residue,
H represents a histidine residue,
Xaa1 represents a lysine residue, a cysteine residue, an aspartic acid residue, a glutamic acid residue, 2-aminosuberic acid, or diaminopropionic acid,
G represents a glycine residue,
Xaa2 represents a glutamic acid residue, a glutamine residue, or an asparagine residue,
L represents a leucine residue,
V represents a valine residue, and
W represents a tryptophan residue, and
the two cysteine residues may be disulfide-bonded or bound to each other via a linker, and the C terminus may be amidated,
and $L_1$-$L_2$-$L_3$     (III)

wherein
$L_1$ represents a polyethylene glycol linker bound to the N terminus of the IgG-binding peptide,
$L_2$ represents an amino acid sequence consisting of 0 or more and 5 or less amino acid residues, and
$L_3$ represents a group having a DBCO group at the terminus,
and
wherein the compound is bound to the polypeptide by a click reaction between the azide group in the formula (II) and the DBCO group in the formula (III).

10. A compound represented by the following formula (II):

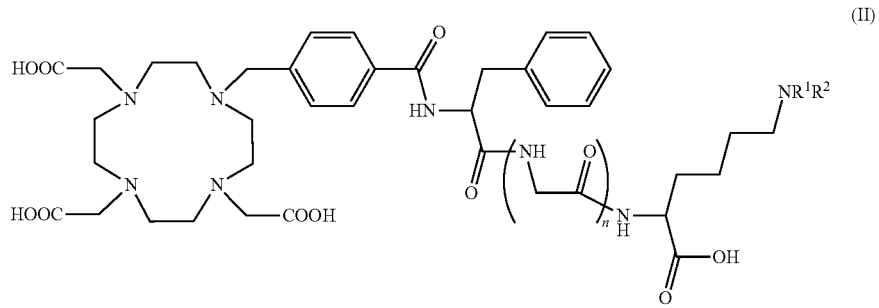

wherein n is 0 or 1, one of $R^1$ and $R^2$ represents a hydrogen atom and the other represents a group represented by $CO(CH_2)_mN_3$ where m is an integer 1 to 10, to which a polypeptide to be bound to a target molecule is bound, or a salt thereof, wherein
the polypeptide is an IgG antibody to which a modified IgG-binding peptide is bound, wherein the modified IgG-binding peptide comprises:
an IgG-binding peptide comprising an amino acid sequence represented by the following formula (I) which consists of 13 to 17 amino acid residues, and
a modification linker represented by the following formula (III) that is bound to the N terminus of the IgG-binding peptide, $(X_{1-3})$-C-$(X_2)$-H-(Xaa1)-G-(Xaa2)-L-V-W-C-$(X_{1})$(SEQ ID NO: 6), wherein
each X independently represents an amino acid residue other than cysteine,
C represents a cysteine residue, H represents a histidine residue, Xaa1 represents a lysine residue, a cysteine residue, an aspartic acid residue, a glutamic acid residue, 2-aminosuberic acid, or diaminopropionic acid, G represents a glycine residue, Xaa2 represents a glutamic acid residue, a glutamine residue, or an asparagine residue, L represents a leucine residue, V represents a valine residue, and W represents a tryptophan residue, and the two cysteine residues may be disulfide-bonded or bound to each other via a linker, and the C terminus may be amidated, and $$L_1\text{-}L_2\text{-}L_3 \qquad (III)$$

wherein $L_1$ represents a polyethylene glycol linker bound to the N terminus of the IgG-binding peptide, $L_2$ represents an amino acid sequence consisting of 0 or more and 5 or less amino acid residues, and $L_3$ represents a group having a DBCO group at the terminus, and wherein the compound is bound to the polypeptide by a click reaction between the azide group in the formula (II) and the DBCO group in the formula (III).

* * * * *